(12) United States Patent
Riina et al.

(10) Patent No.: US 8,932,326 B2
(45) Date of Patent: Jan. 13, 2015

(54) METHOD AND APPARATUS FOR REPAIRING VASCULAR ABNORMALITIES AND/OR OTHER BODY LUMEN ABNORMALITIES USING AN ENDOLUMINAL APPROACH AND A FLOWABLE FORMING MATERIAL

(75) Inventors: Howard Riina, Scarsdale, NY (US); Jeffrey Milsom, New York, NY (US); J. Fredrick Cornhill, New York, NY (US); Robert R. Andrews, Norfolk, MA (US); Clair L. Strohl, Norfolk, MA (US); Edward L. Dickinson, Littleton, MA (US)

(73) Assignee: Cornell University, Ithaca, NY (US)

( * ) Notice: Subject to any disclaimer, the term of this patent is extended or adjusted under 35 U.S.C. 154(b) by 1135 days.

(21) Appl. No.: 12/482,218

(22) Filed: Jun. 10, 2009

(65) Prior Publication Data

US 2010/0076484 A1 Mar. 25, 2010

Related U.S. Application Data

(60) Provisional application No. 61/189,670, filed on Aug. 21, 2008, provisional application No. 61/131,584, filed on Jun. 10, 2008.

(51) Int. Cl.
*A61B 17/08* (2006.01)
*A61M 31/00* (2006.01)
*A61F 2/958* (2013.01)
(Continued)

(52) U.S. Cl.
CPC ............ *A61F 2/958* (2013.01); *A61M 25/1011* (2013.01); *A61M 29/02* (2013.01); *A61F 2/945* (2013.01); *A61F 2002/30583* (2013.01); *A61F 2002/823* (2013.01); *A61F 2210/0085* (2013.01); *A61M 2025/1052* (2013.01)
USPC .... 606/214; 604/101.03; 604/509; 604/96.01

(58) Field of Classification Search
USPC ......... 606/213, 200, 191–195, 214, 108, 158, 606/28; 604/509, 101.01, 101.03, 101.05, 604/96.01; 623/1.13, 23.72
See application file for complete search history.

(56) References Cited

U.S. PATENT DOCUMENTS

| 4,183,102 A | 1/1980 | Guiset |
| 4,423,725 A * | 1/1984 | Baran et al. ............. 128/207.15 |

(Continued)

FOREIGN PATENT DOCUMENTS

| WO | WO 95/05209 | 2/1995 |
| WO | WO 98/08558 | 3/1998 |
| WO | WO 00/74749 | 12/2000 |

*Primary Examiner* — Ashley Fishback
*Assistant Examiner* — Jing Ou
(74) *Attorney, Agent, or Firm* — Pandiscio & Pandiscio

(57) ABSTRACT

Apparatus and method for repairing an abnormality in the wall of a body lumen, the method comprising isolating the abnormality in the wall of the body lumen from flow in the body lumen; positioning flowable forming material adjacent to the abnormality in the wall of the body lumen; and transforming the flowable forming material into a substantially stationary state so as to repair the abnormality in the wall of the body lumen, and the apparatus comprising a supply of flowable forming material; zone isolation apparatus for isolating the abnormality in the wall of the body lumen from flow in the body lumen; and positioning apparatus for positioning the flowable forming material adjacent to the abnormality in the wall of the body lumen so as to repair the abnormality in the wall of the body lumen.

37 Claims, 22 Drawing Sheets

(51) Int. Cl.
  *A61M 25/10* (2013.01)
  *A61M 29/02* (2006.01)
  A61F 2/945 (2013.01)
  A61F 2/30 (2006.01)
  A61F 2/82 (2013.01)

(56) References Cited

U.S. PATENT DOCUMENTS

| | | | | |
|---|---|---|---|---|
| 4,447,227 A * | 5/1984 | Kotsanis | | 604/95.03 |
| 4,456,011 A | 6/1984 | Warnecke | | |
| 4,636,195 A * | 1/1987 | Wolinsky | | 604/509 |
| 4,832,688 A | 5/1989 | Sagae et al. | | |
| 5,135,484 A | 8/1992 | Wright | | |
| 5,287,857 A | 2/1994 | Mann | | |
| 5,342,306 A * | 8/1994 | Don Michael | | 604/101.04 |
| 5,405,322 A * | 4/1995 | Lennox et al. | | 606/28 |
| 5,514,092 A | 5/1996 | Forman et al. | | |
| 5,554,119 A | 9/1996 | Harrison et al. | | |
| 5,556,389 A | 9/1996 | Liprie | | |
| 5,558,642 A * | 9/1996 | Schweich et al. | | 604/103.01 |
| 5,674,198 A | 10/1997 | Leone | | |
| 5,716,340 A | 2/1998 | Schweich, Jr. et al. | | |
| 5,728,068 A * | 3/1998 | Leone et al. | | 604/101.01 |
| 5,776,097 A * | 7/1998 | Massoud | | 604/500 |
| 5,843,156 A | 12/1998 | Slepian et al. | | |
| 6,139,517 A | 10/2000 | Macoviak et al. | | |
| 6,214,022 B1 | 4/2001 | Taylor et al. | | |
| 6,287,321 B1 | 9/2001 | Jang | | |
| 6,299,597 B1 * | 10/2001 | Buscemi et al. | | 604/101.03 |
| 6,592,566 B2 * | 7/2003 | Kipke et al. | | 604/508 |
| 6,692,486 B2 * | 2/2004 | Jaafar et al. | | 606/7 |
| 6,913,610 B2 | 7/2005 | Nakao | | |
| 6,936,057 B1 * | 8/2005 | Nobles | | 606/194 |
| 7,105,031 B2 | 9/2006 | Letort | | |
| 7,819,841 B2 * | 10/2010 | Horrigan | | 604/104 |
| 8,147,449 B2 | 4/2012 | Gobel et al. | | |
| 2002/0026217 A1 * | 2/2002 | Baker et al. | | 606/223 |
| 2003/0088246 A1 | 5/2003 | Swartz et al. | | |
| 2003/0135264 A1 * | 7/2003 | Whalen et al. | | 623/1.15 |
| 2003/0212427 A1 * | 11/2003 | Truckai et al. | | 606/195 |
| 2004/0068226 A1 | 4/2004 | Brannon | | |
| 2004/0215124 A1 | 10/2004 | Yamasaki et al. | | |
| 2004/0225251 A1 | 11/2004 | Glickman | | |
| 2005/0085770 A1 | 4/2005 | Don Michael | | |
| 2005/0131458 A1 * | 6/2005 | Batich et al. | | 606/214 |
| 2005/0186242 A1 | 8/2005 | Hunter et al. | | |
| 2005/0245893 A1 * | 11/2005 | Leschinsky | | 604/509 |
| 2005/0267407 A1 | 12/2005 | Goldman | | |
| 2006/0200191 A1 | 9/2006 | Zadno-Azizi | | |
| 2007/0213761 A1 | 9/2007 | Murphy et al. | | |
| 2008/0033341 A1 * | 2/2008 | Grad | | 604/20 |
| 2008/0045996 A1 * | 2/2008 | Makower et al. | | 606/194 |

* cited by examiner

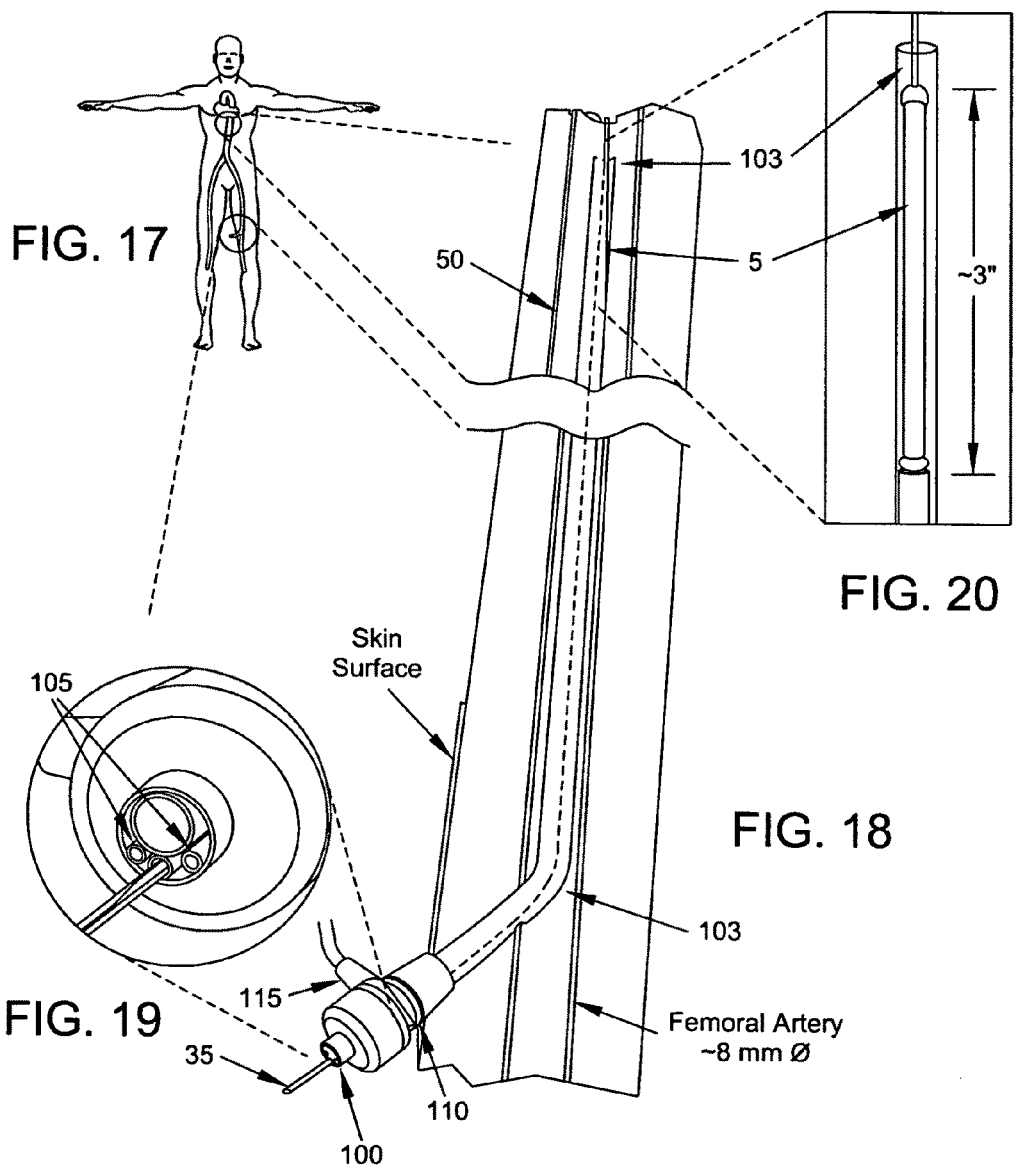

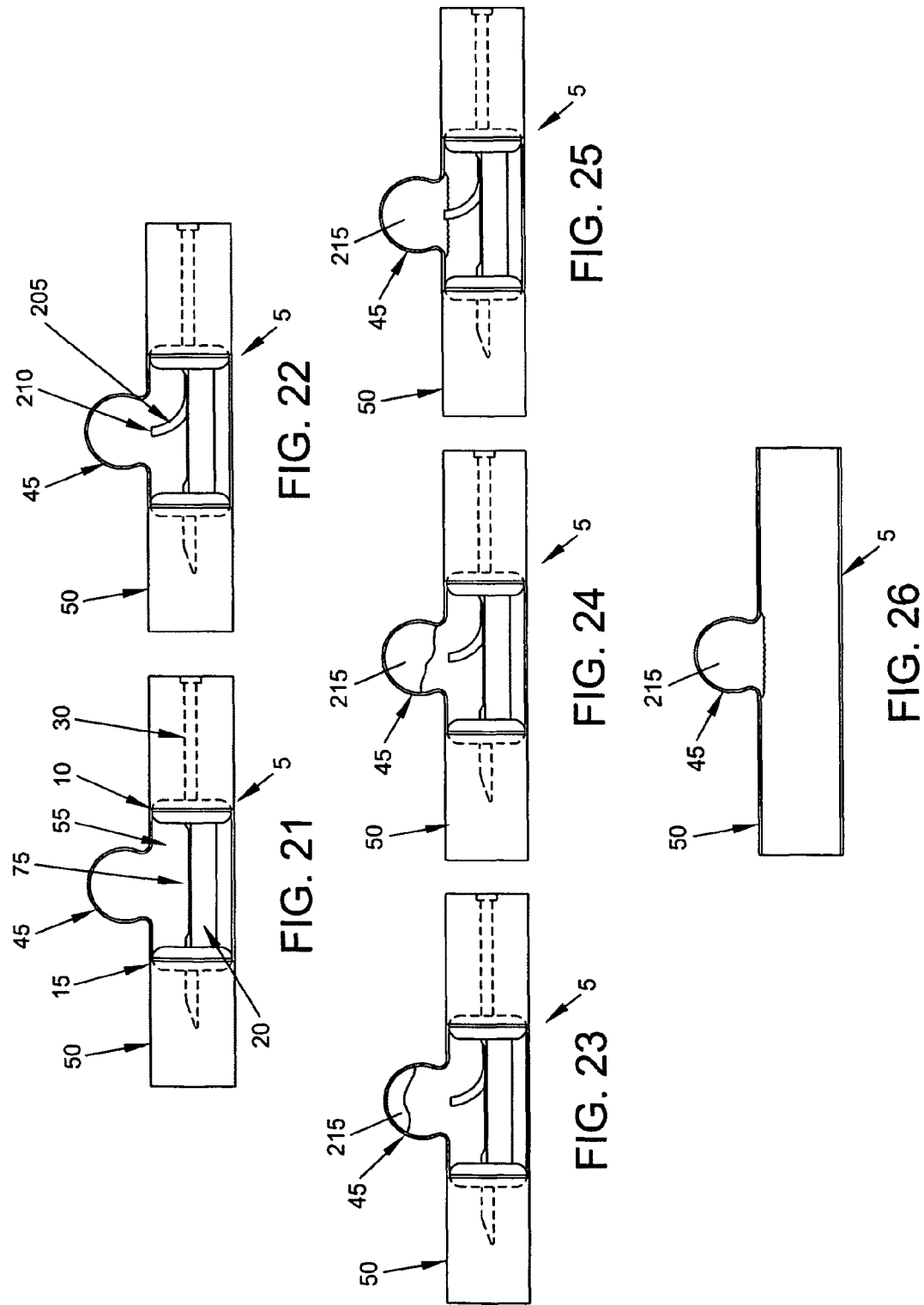

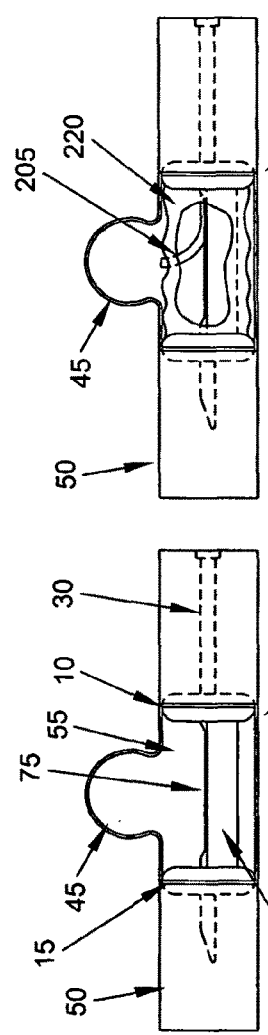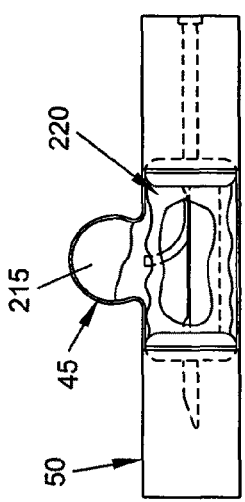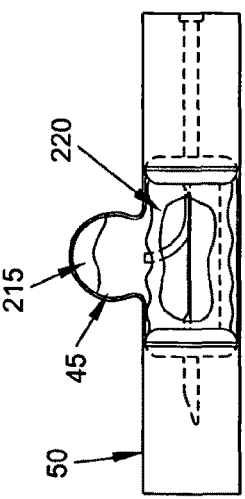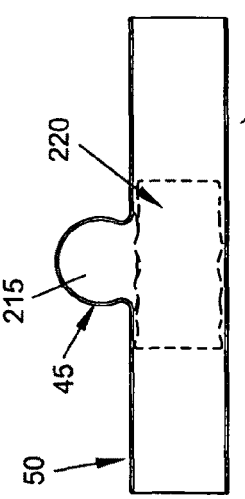

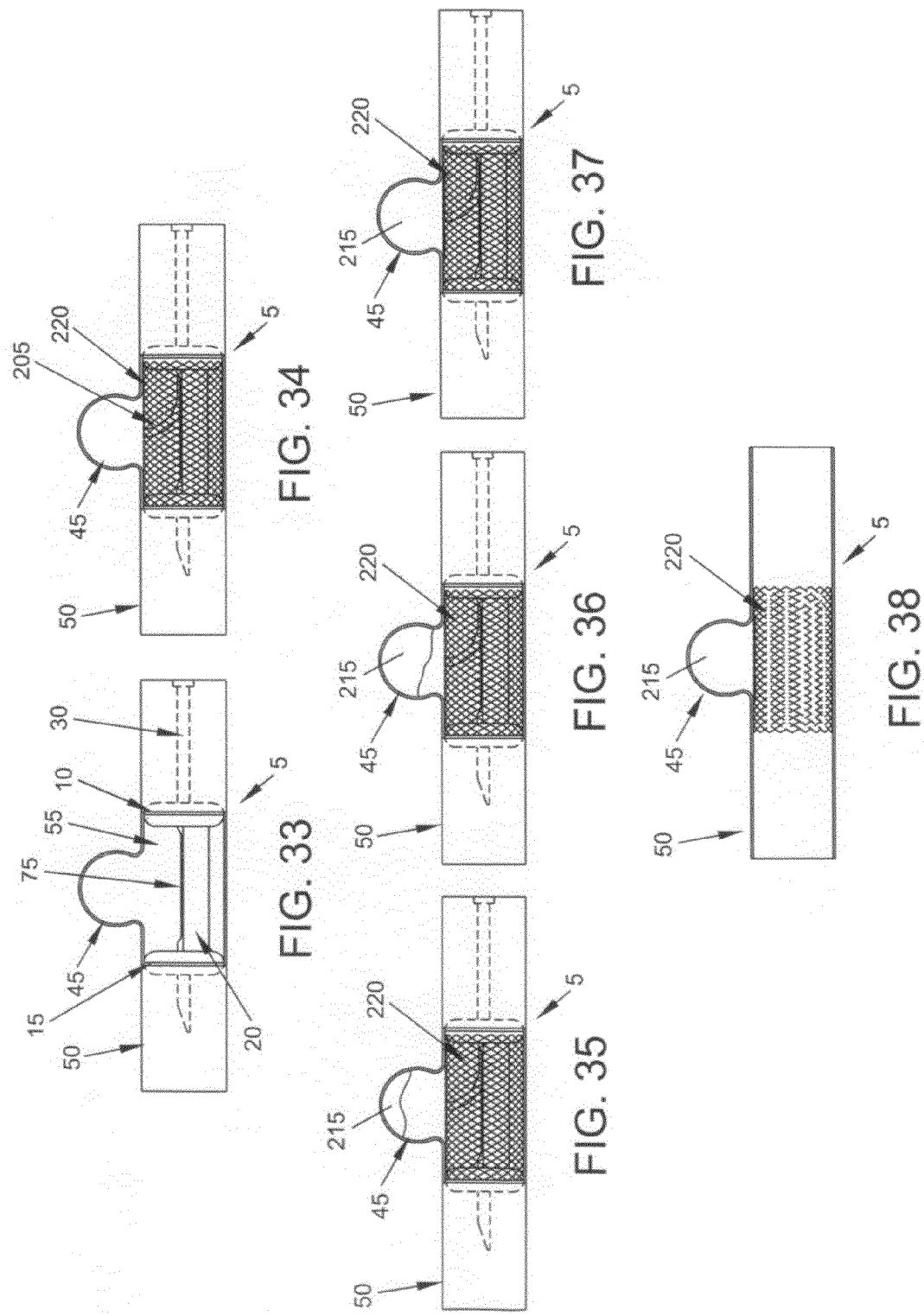

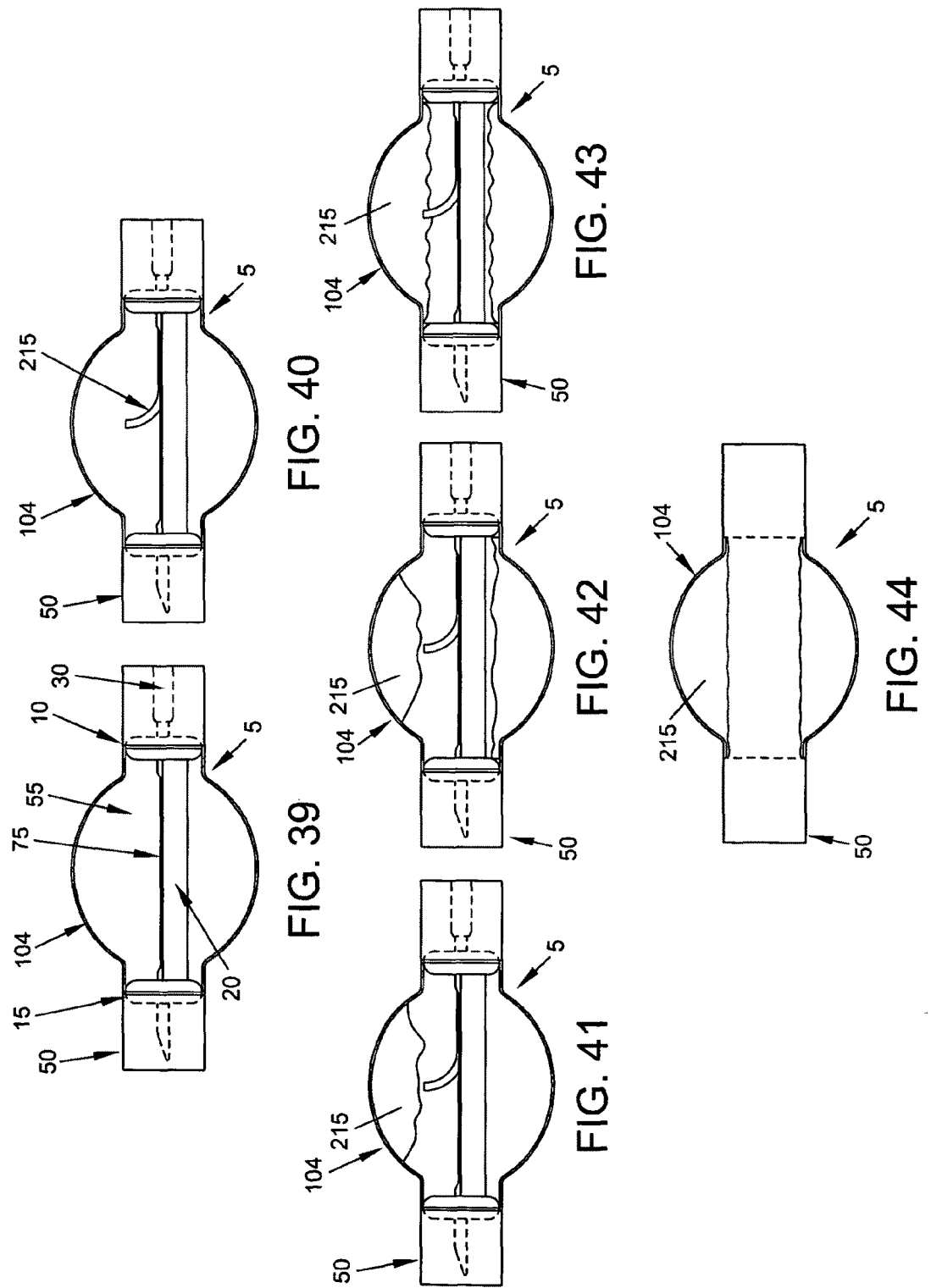

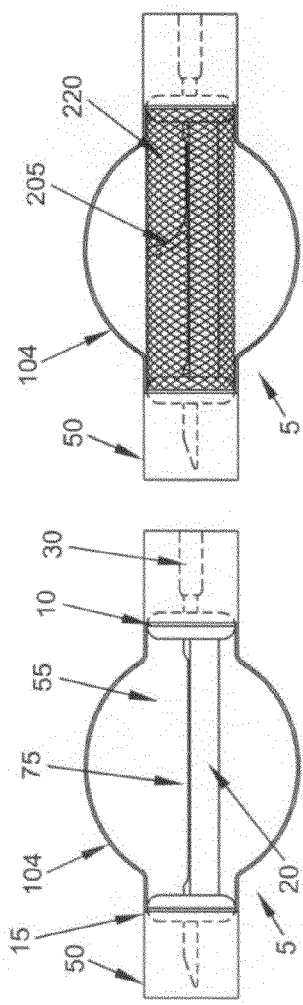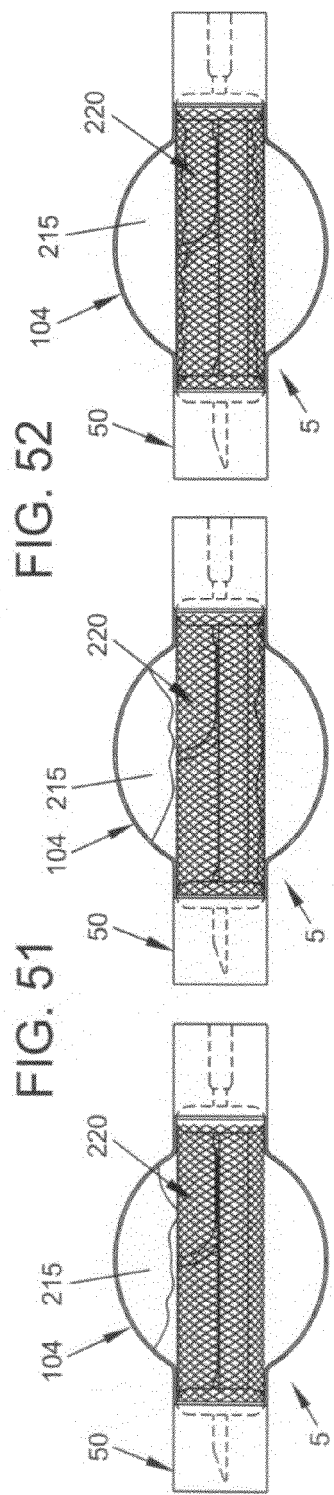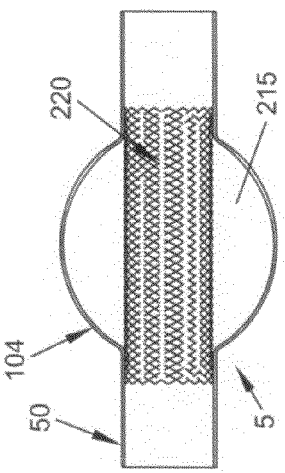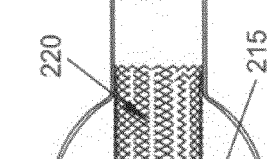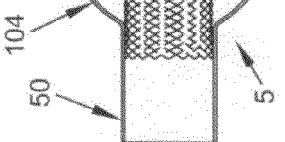

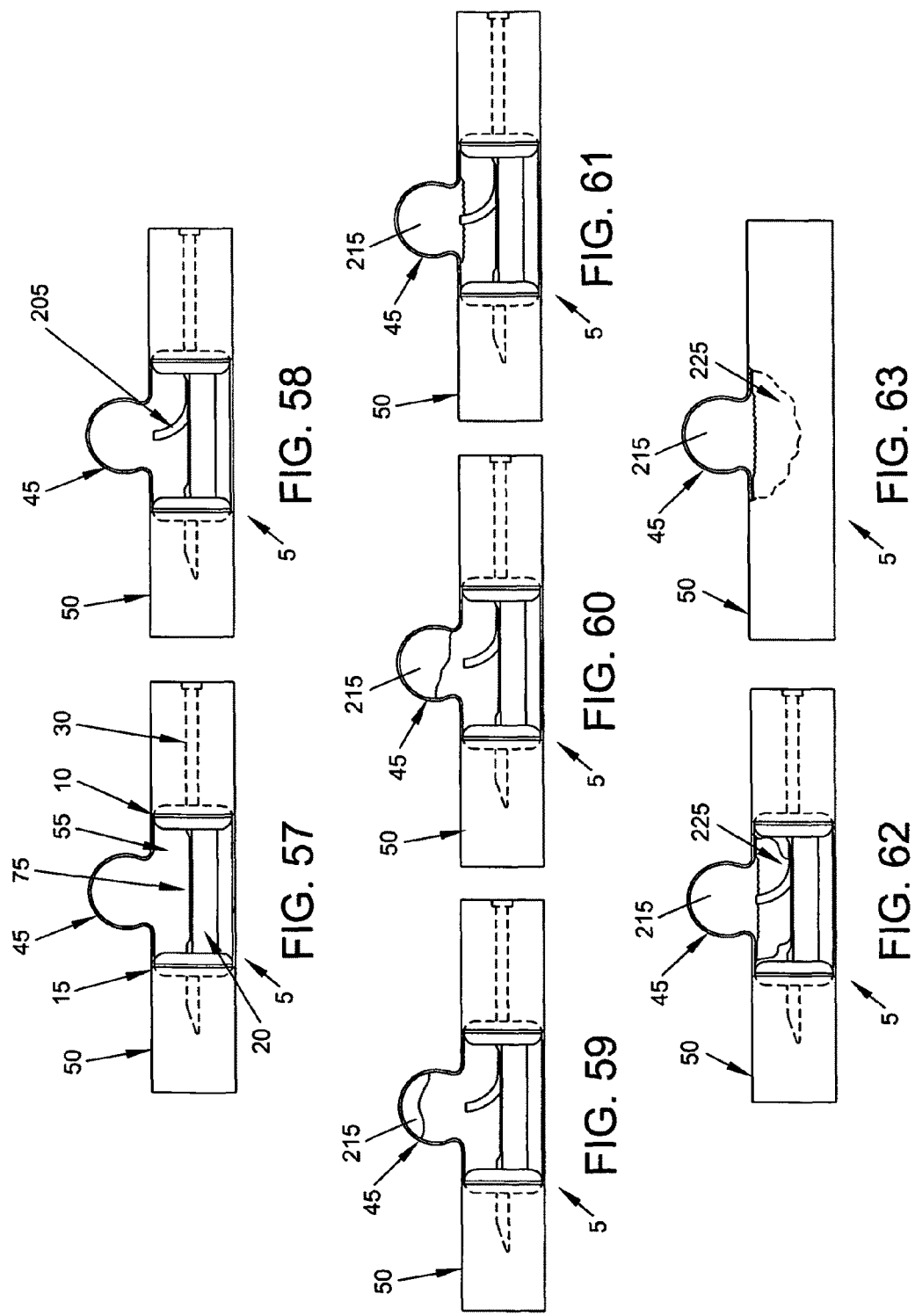

METHOD AND APPARATUS FOR REPAIRING VASCULAR ABNORMALITIES AND/OR OTHER BODY LUMEN ABNORMALITIES USING AN ENDOLUMINAL APPROACH AND A FLOWABLE FORMING MATERIAL

REFERENCE TO PENDING PRIOR PATENT APPLICATIONS

This patent application claims benefit of:
(i) prior U.S. Provisional Patent Application Ser. No. 61/189,670, filed Aug. 21, 2008 by Howard Riina et al. for METHOD AND APPARATUS FOR ACCESSING THE SIDE WALL OF A VASCULAR STRUCTURE OR OTHER BODY LUMEN, ORGAN OR TUBULAR STRUCTURE WHILE SIMULTANEOUSLY PROVIDING ZONE ISOLATION AND BYPASS CAPABILITY; and
(ii) prior U.S. Provisional Patent Application Ser. No. 61/131,584, filed Jun. 10, 2008 by Howard Riina et al. for INJECTABLE MOLD.

The two above-identified patent applications are hereby incorporated herein by reference.

FIELD OF THE INVENTION

This invention relates to medical procedures and apparatus in general, and more particularly to medical procedures and apparatus for accessing the wall of a vascular structure or other body lumen.

BACKGROUND OF THE INVENTION

Medical technologies are now expanding so that curative therapies may now be applied directly to the wall of a vascular structure or other body lumen (e.g., tubular structure or organ) within the human body. In most situations it will be necessary to access the inside (or other portion) of the wall of a vascular structure or other body lumen in order to provide therapy to a patient. By way of example but not limitation, it may be necessary to treat an aneurysm formed in the wall of an artery (e.g., a lateral aneurysm such as a saccular aneurysm, a fusiform aneurysm such as a typical abdominal aortic aneurysm), or to treat a lesion formed on the wall of a vascular structure (e.g., an artery or vein) or other tubular or hollow structure. As used herein, the term "vascular structure" is intended to encompass any tubular or hollow structure of the vasculature (e.g., an artery, a vein, a blood chamber, etc.), and the term "body lumen" is intended to encompass any tubular or hollow structure, including the gastrointestinal or genitourinary tracts, the lymph system, an air passageway, the interior of a hollow organ, a passageway through a body structure, etc. As used herein, the term "wall" of a vascular structure or other body lumen is intended to encompass the inside surface of the wall and/or any other portion of the wall, including aneurysms, lesions, etc. which may be formed in or on the wall.

Additionally, in many situations it may be desirable to isolate a segment of the vascular structure (or other body lumen) from the remainder of the vascular structure (or other body lumen). By way of example but not limitation, a particular therapy applied to the inside of the wall of a vascular structure may create debris which should be localized and prevented from flowing downstream from the site of the therapy.

Furthermore, in many situations it may become necessary to apply therapy to the inside of the wall of a vascular structure (or other body lumen) without interrupting the flow of blood (or other fluids) through the vascular structure (or other body lumen).

Thus, there is a substantial need for a novel method and apparatus for accessing the wall of a vascular structure or other body lumen while simultaneously providing "zone isolation" and simultaneously providing fluid bypass capability. Ideally, pressure and fluid (presence or absence) should be controllable within the isolation zone, thereby facilitating the use of medical instruments (including cutting instruments, biopsy instruments, closure instruments, endoscopic visualization, etc.), vacuum, electrical energy (e.g., electrosurgery), adhesives and/or other therapies which may be difficult to apply in a zone where blood or any other biologic fluid or substance is present and/or flowing.

SUMMARY OF THE INVENTION

The present invention provides a novel method and apparatus for accessing the wall of a vascular structure or other body lumen while simultaneously providing zone isolation and simultaneously providing fluid bypass capability.

In one preferred form of the invention, the novel method and apparatus permits pressure and fluid (presence or absence) to be controllable within the isolation zone, thereby facilitating the use of medical instruments (including cutting instruments, biopsy instruments, closure instruments, material delivery systems, endoscopes, etc.), vacuum, electrical energy (e.g., electrosurgery), adhesives and/or other therapies (e.g., agents promoting thrombus, gene therapeutic agents, etc.) which may be difficult to apply in a zone where blood or another biologic fluid or substance is present and/or flowing.

More particularly, the present invention comprises the provision and use of an access system comprising an erectable proximal isolation barrier (e.g., a balloon, a superelastic shape memory alloy ring, etc.), an erectable distal isolation barrier (e.g., a balloon, a superelastic shape memory alloy ring, etc.), and a bypass channel extending between the proximal isolation barrier and the distal isolation barrier, such that when the access system is erected in a body lumen, the access system can isolate a segment of the body lumen from the remainder of the body lumen, while still permitting a fluid to flow independently through the isolated segment of the body lumen. Additionally, the access system preferably comprises a working catheter extending through the proximal isolation barrier and providing access (e.g., for instruments, etc.) to the wall of the isolated segment of the body lumen. Furthermore, the access system can be configured so as to be mountable on a guidewire, so that the access system can be delivered over a guidewire to a desired position within a body lumen.

In one preferred form of the present invention, there is provided apparatus for accessing the wall of a body lumen while simultaneously providing zone isolation and fluid bypass capability, the apparatus comprising:

an erectable proximal isolation barrier capable of making a sealing engagement with the wall of the body lumen;

an erectable distal isolation barrier capable of making a sealing engagement with the wall of the body lumen;

a bypass channel secured to, and extending between, the proximal isolation barrier and the distal isolation barrier, the bypass channel comprising a lumen communicating with the region proximal to the proximal isolation barrier and with the region distal to the distal isolation barrier; and a working catheter passing through the proximal isolation barrier and terminating short of the distal isolation barrier, the working catheter providing a central lumen for providing access to the wall of the body lumen between the proximal isolation barrier and the distal isolation barrier.

In another preferred form of the present invention, there is provided a method for accessing the wall of a body lumen while simultaneously providing zone isolation and fluid bypass capability, the method comprising:

providing an access system comprising:
an erectable proximal isolation barrier capable of making a sealing engagement with the wall of the body lumen;
an erectable distal isolation barrier capable of making a sealing engagement with the wall of the body lumen;
a bypass channel secured to, and extending between, the proximal isolation barrier and the distal isolation barrier, the bypass channel comprising a lumen communicating with the region proximal to the proximal isolation barrier and with the region distal to the distal isolation barrier; and
a working catheter passing through the proximal isolation barrier and terminating short of the distal isolation barrier, the working catheter providing a central lumen for providing access to the wall of the body lumen between the proximal isolation barrier and the distal isolation barrier;

deploying the access system within the body lumen;
erecting the distal isolation barrier and the proximal isolation barrier; and
accessing the wall of the body lumen through the working catheter.

As noted above, the present invention provides a novel method and apparatus for accessing the wall of a vascular structure or other body lumen while simultaneously providing zone isolation and fluid bypass capability. In the following description, the present invention may sometimes hereinafter be discussed in the context of application to a vascular structure, however, it should be appreciated that this is done solely for the sake of clarity of illustration and should not be considered as limiting the scope of the present invention. Thus, the present invention may also be used in conjunction with body lumens other than vascular structures, e.g., the gastrointestinal or genitourinary tract, the lymph system, an air passageway, the interior of a hollow organ, a passageway through a body structure, etc.

In another preferred form of the present invention, there is provided a method for repairing an abnormality in the wall of a body lumen, the method comprising:

isolating the abnormality in the wall of the body lumen from flow in the body lumen;
positioning flowable forming material adjacent to the abnormality in the wall of the body lumen; and
transforming the flowable forming material into a substantially stationary state so as to repair the abnormality in the wall of the body lumen.

In another preferred form of the present invention, there is provided apparatus for repairing an abnormality in the wall of a body lumen, the apparatus comprising:

a supply of flowable forming material;
zone isolation apparatus for isolating the abnormality in the wall of the body lumen from flow in the body lumen; and
positioning apparatus for positioning the flowable forming material adjacent to the abnormality in the wall of the body lumen so as to repair the abnormality in the wall of the body lumen.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 13, 14, 14A and 15-20 illustrate a delivery catheter which may used to deploy the access system of the present invention at a procedure site within a vascular structure;

FIGS. 21-26 are schematic views showing one approach for repairing a lateral aneurysm using an endoluminal approach and a flowable forming material;

FIGS. 27-32 are schematic views showing another approach for repairing a lateral aneurysm using an endoluminal approach and a flowable forming material;

FIGS. 33-38 are schematic views showing still another approach for repairing a lateral aneurysm using an endoluminal approach and a flowable forming material;

FIGS. 39-44 are schematic views showing an approach for repairing a fusiform aneurysm using an endoluminal approach and a flowable forming material;

FIGS. 51-56 are schematic views showing still another approach for repairing a fusiform aneurysm using an endoluminal approach and a flowable forming material;

FIGS. 57-63 are schematic views showing another approach for repairing a lateral aneurysm using an endoluminal approach and a flowable forming material;

DETAILED DESCRIPTION OF THE PREFERRED EMBODIMENTS

Figure 1:
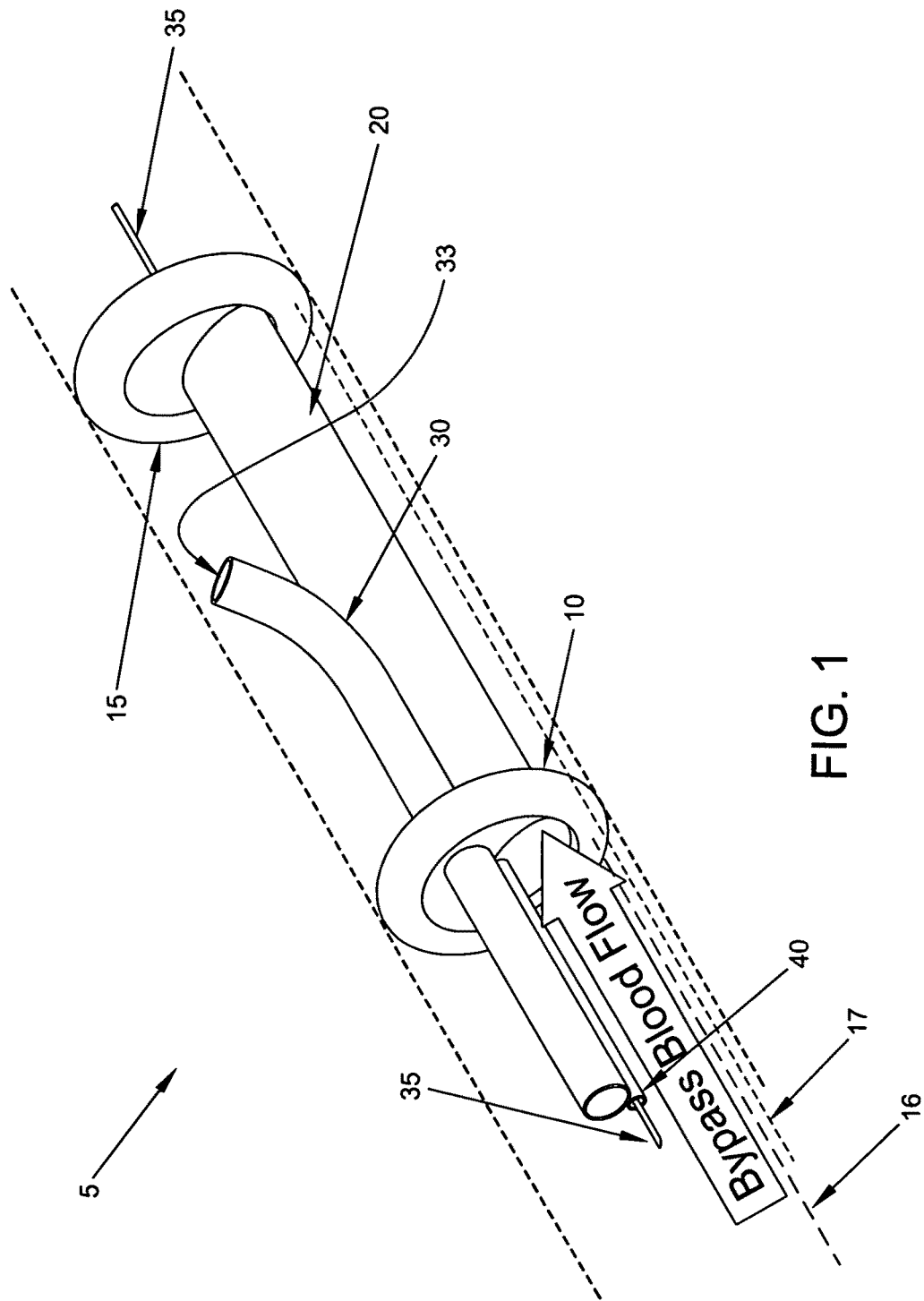
FIG. 1 is a schematic perspective view showing the access system of the present invention deployed within a vascular structure.
Figure 2:
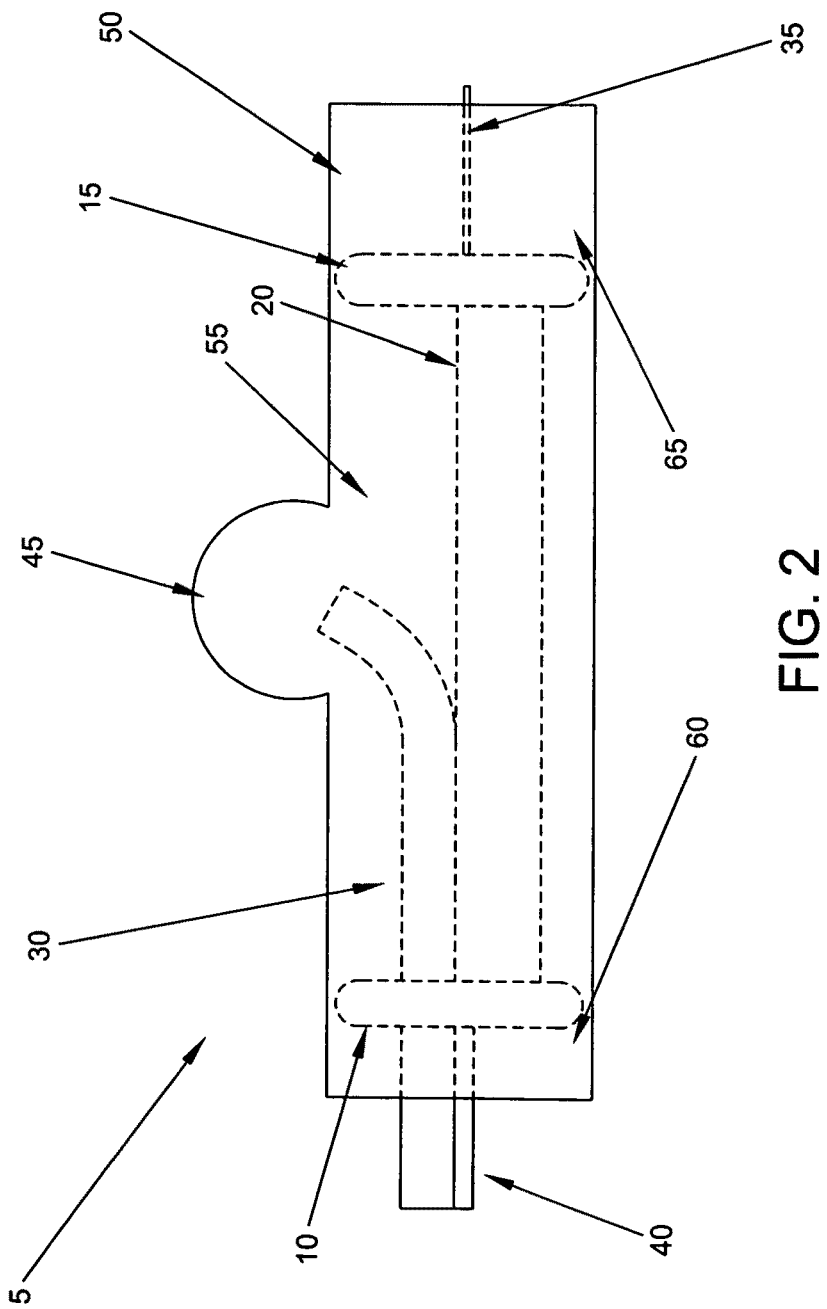
FIG. 2 is a schematic side view showing the access system of FIG. 1 deployed within a vascular structure, wherein the vascular structure includes an aneurysm.
Figure 3:
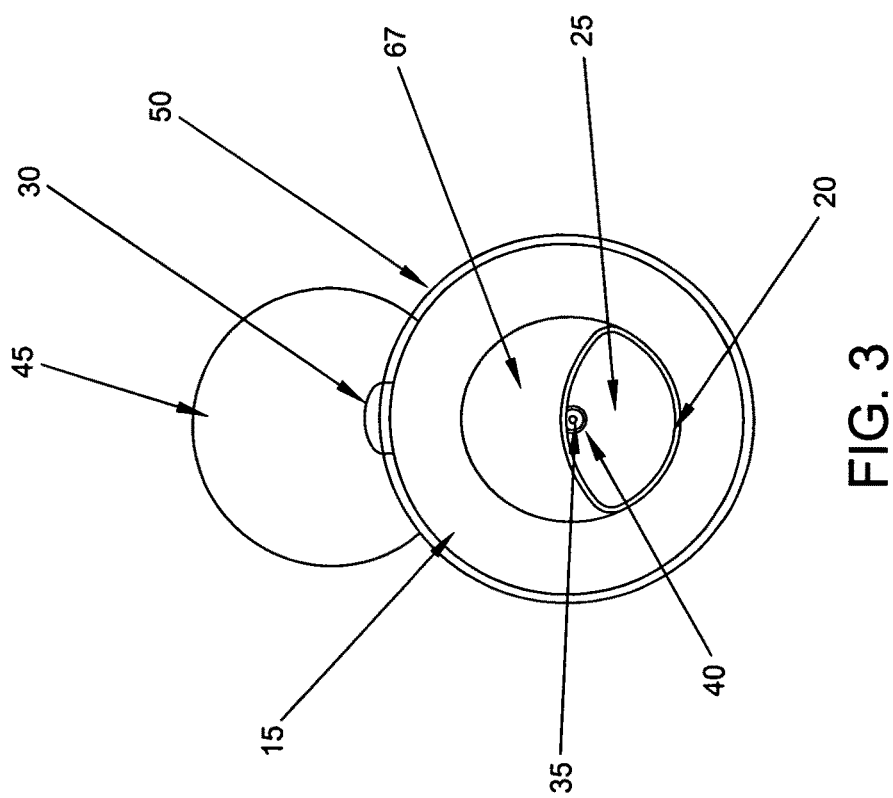
FIG. 3 is a schematic end view, as seen from the distal end, showing the access system of FIG. 1 deployed within the vascular structure shown in FIG. 2.

Method and Apparatus for Accessing the Wall of a Vascular Structure or Other Body Lumen while Simultaneously Providing Zone Isolation and Fluid Bypass Capability Looking first at FIGS. 1-3, there is shown an access system 5 formed in accordance with the present invention. Access system 5 generally comprises an erectable proximal isolation barrier 10 and an erectable distal isolation barrier 15 for disposition within the lumen of a vascular structure or other body lumen. Erectable proximal isolation barrier 10 and erectable distal isolation barrier 15 are formed so that they can (i) initially assume a diametrically-reduced configuration so as to facilitate insertion of access system 5 to a site where a procedure (e.g., therapy, diagnosis, exploration, etc.) is to be conducted, and (ii) thereafter assume a diametrically-expanded configuration once at the procedure site so as to form a fluid-tight (occlusive) seal against the wall of the vascular structure, whereby to isolate a segment of the vascular structure from the remainder of the vascular structure, e.g., while a procedure is performed. In one preferred form of the invention, proximal isolation barrier 10 and distal isolation barrier 15 have a peripheral surface texture to help ensure that the barriers will maintain their position in the vascular structure once deployed. By way of example but not limitation, such peripheral surface texturing may comprise dimpling, circumferential ribbing, etc. In this respect it will be appreciated that the proximal and distal isolation barriers should remain in place when systolic pressure is present on the outer surfaces of each of the isolation barriers and atmospheric pressure is present within the isolated segment of the vascular structure. Furthermore, erectable proximal isolation barrier 10 and erectable distal isolation barrier 15 are formed so that they may be collapsed when desired so as to facilitate removal of access system 5 from the vascular structure, e.g., at the conclusion of the procedure. By way of example but not limitation, erectable proximal isolation barrier 10 and erectable distal isolation barrier 15 may be formed by inflatable/deflatable balloons, compressible/expandable superelastic shape memory alloy (e.g., Nitinol) rings, etc. As a result of this construction, when access system 5 has been deployed at a desired point in a vascular structure or other body lumen, and erectable proximal isolation barrier 10 and erectable distal isolation barrier 15 have been expanded to their sealing condition, access system 5 can isolate a segment of the vascular structure (i.e., the portion located between erected proximal isolation barrier 10 and erected distal isolation barrier 15) from the remainder of the vascular structure, e.g., while a procedure is performed. This can be important in a variety of situations, e.g., where the procedure may dislodge debris which could harm downstream tissue.

Access system 5 is preferably constructed so that erectable proximal isolation barrier 10 and erectable distal isolation barrier 15 may be diametrically-expanded and diametrically-reduced independently of one another. In other words, access system 5 is preferably constructed so that proximal isolation barrier 10 may be diametrically-expanded or diametrically-reduced regardless of the condition of distal isolation barrier 15, and vice-versa.

Where erectable proximal isolation barrier 10 and erectable distal isolation barrier 15 are formed out of an inflatable/deflatable balloon, access system 5 also comprises channels for delivering fluid (a liquid or a gas) for inflating/deflating the balloons. By way of example but not limitation, a channel 16 may be provided for inflating the balloon of erectable proximal isolation barrier 10 and a channel 17 may be provided for inflating the balloon of erectable distal isolation barrier 15.

Access system 5 further comprises a bypass channel 20 secured to, and extending between and through, proximal isolation barrier 10 and distal isolation barrier 15. Bypass channel 20 comprises a central lumen 25 (FIG. 3) which opens proximal to proximal isolation barrier 10 and distal to distal isolation barrier 15, whereby to permit flow from one side of access system 5 to the other side of access system 5. As a result of this construction, when access system 5 is deployed in a vascular structure so as to isolate a segment of the vascular structure from the remainder of the vascular structure, access system 5 can still permit blood to flow uninterrupted through the bypass channel 20 which traverses the isolated segment of the vascular structure. This can be important in a variety of situations, e.g., such as where continued blood flow is important for the oxygenation of downstream tissues.

In one embodiment, the upstream isolation barrier may be configured so as to channel blood flow into bypass channel 20. Thus, for example, in FIG. 1, proximal isolation barrier 10 may be configured so as to channel blood flow into bypass channel 20. By way of example but not limitation, the upstream side of proximal isolation barrier 10 may be formed with a concave (e.g., funnel-shaped) surface surrounding the entrance to bypass channel 20.

Thus it will be seen that access system 5 provides both zone isolation (via proximal isolation barrier 10 and distal isolation barrier 15) and distal perfusion (via bypass channel 20). These features can be important in a variety of situations where zone isolation and distal perfusion are both desirable and/or necessary, e.g., where vascular trauma needs to be temporarily stabilized while the patient is transported to another site for further treatment, where an aneurysm (e.g., abdominal or thoracic, iliac or femoral, etc.) is bleeding and/or threatening to rupture, or actually has ruptured, etc. Furthermore, it should be appreciated that access system 5 may be used on both the arterial and venous sides of the circulation system.

Access system 5 further comprises a working catheter 30 which passes through proximal isolation barrier 10 and provides access (e.g., for medical instruments including but not limited to cutting instruments, biopsy instruments, closure instruments, material delivery systems, endoscopes, etc., including for the delivery of adhesives and/or agents for promoting thrombus, gene therapeutic agents, etc.) to the wall of the isolated length of the vascular structure. Preferably, working catheter 30 can slide forward and backward through proximal isolation barrier 10 such that working catheter 30 can be positioned anywhere between proximal isolation barrier 10 and distal isolation barrier 15. Additionally, access system 5 is preferably configured so that working catheter 30 can be rotated in order that the distal tip 33 of working catheter 30 can access substantially the entire circumference of the isolated vessel.

Access system 5 is preferably configured so as to be mountable on a guidewire 35, so that access system 5 may be delivered to a desired position within the vascular structure. By way of example but not limitation, access system 5 may comprise a guidewire channel 40 mounted to proximal isolation barrier 10 and/or working catheter 30 (e.g., proximal to proximal isolation barrier 10, as shown in FIG. 1), such that guidewire 35 may be received within bypass channel 20 and guidewire channel 40, whereby to permit controlled delivery of access system 5 to a desired location within a vascular structure.

In one preferred form of use, and looking now at FIGS. 1-3, access system 5 may be used to isolate, bypass and access the wall of a vascular structure. By way of example but not limitation, access system 5 may be used to isolate, bypass and access a lateral aneurysm 45 formed in the wall of a vascular structure 50. In this case, guidewire 35 is first deployed down vascular structure 50. Then access system 5, with proximal isolation barrier 10 and distal isolation barrier 15 set in their diametrically-reduced condition, is advanced over the guidewire to a point adjacent to lateral aneurysm 45. Next, proximal isolation barrier 10 and distal isolation barrier 15 are set in their diametrically-expanded condition, so as to conform to, and seal against, the wall of the vascular structure and thereby create an isolation zone 55 which encompasses lateral aneurysm 45. However, it will be appreciated that blood is still able to flow past the isolation zone (e.g., from flow zone 60 to flow zone 65) via bypass channel 20. To the extent that the proximal end of working catheter 30 is open to the atmosphere, blood in the isolation zone may flow out of the isolation zone via the working catheter and be replaced with air. Alternatively, the working catheter may be used to introduce another fluid (e.g., saline) into the isolation zone. At this point, instruments may be advanced through working catheter 30 so as to access, and provide therapy to, lateral aneurysm 45. Such instruments may include, but are not limited to, cutting instruments, biopsy instruments, closure instruments, material delivery systems, endoscopes, etc. At the conclusion of the procedure, proximal isolation barrier 10 and distal isolation barrier 15 are set in their diametrically-reduced condition, and then access system 5 is withdrawn along guidewire 35. Finally, guidewire 35 is removed from vascular structure 50.

Any debris created in isolation zone 55 during the procedure may be removed by withdrawing blood/debris from isolation zone 55. In one form of the invention, blood/debris evacuation may be effected by applying suction via working catheter 30 while both proximal isolation barrier 10 and distal isolation barrier 15 remain erected. In another form of the invention, blood/debris evacuation may be effected by first returning proximal isolation barrier 10 to its diametrically-reduced configuration while retaining distal isolation barrier 15 in its diametrically-expanded configuration, then removing blood/debris via suction, and then returning distal isolation barrier 15 to its diametrically-reduced configuration so that access system 5 may be removed from the vascular structure. This latter approach may be particularly applicable to angioplasty in the coronary and/or carotid arteries.

Figure 4:
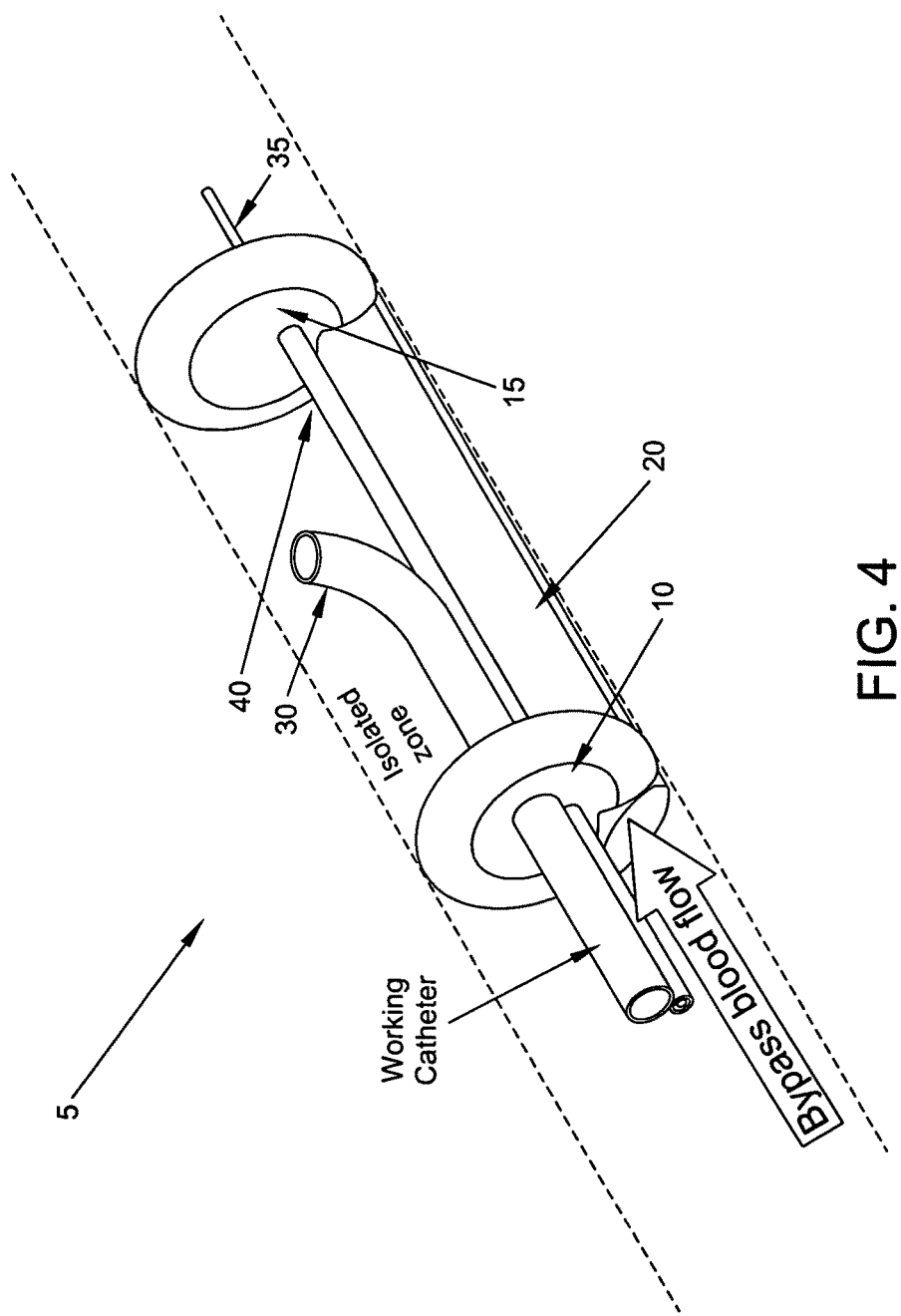
FIG. 4 is a schematic perspective view showing an alternative form of an access system deployed within a vascular structure.
Figure 5:
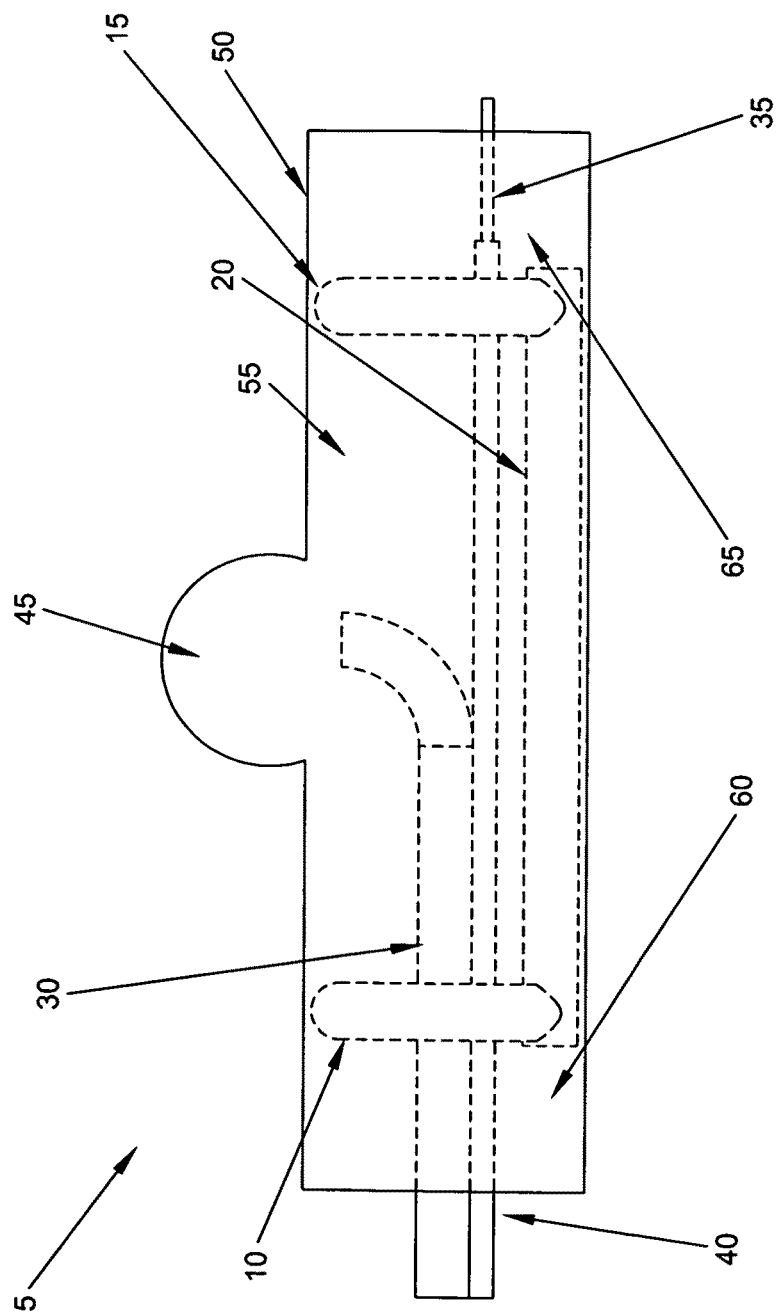
FIG. 5 is a schematic side view showing the access system of FIG. 4 deployed within a vascular structure, wherein the vascular structure includes an aneurysm.
Figure 6:
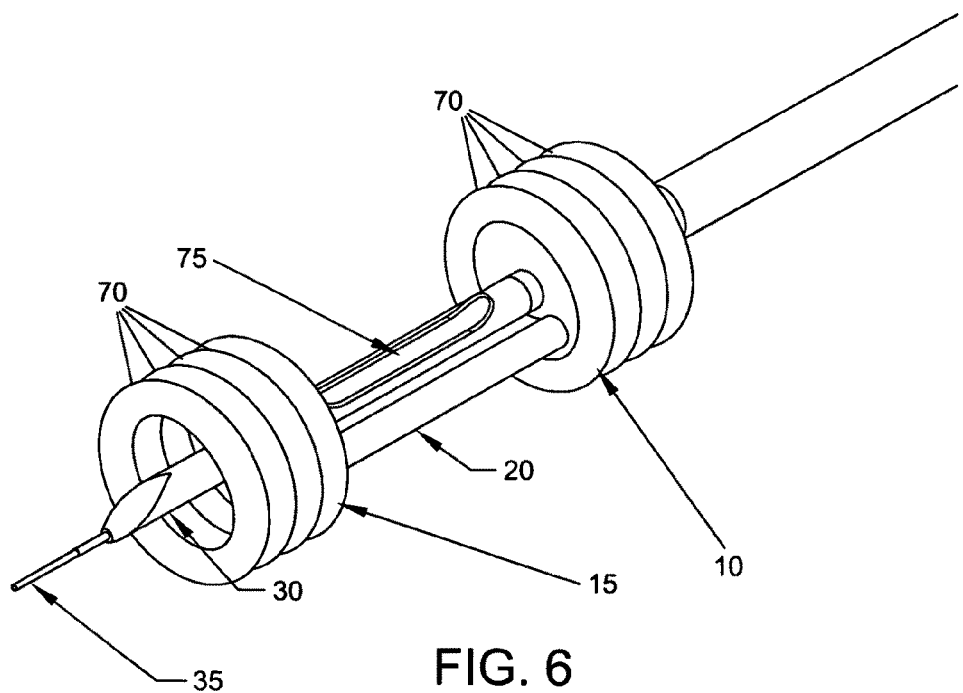
FIG. 6 is a schematic perspective view showing an alternative form of an access system.

FIGS. 4 and 5 show an alternative form of access system 5. The access system shown in FIGS. 4 and 5 is substantially the same as the access system shown in FIGS. 1-3, except that guidewire channel 40 extends parallel to, but spaced from, bypass channel 20 and bypass channel 20 is positioned diametrically outboard so as to sit proximate to the wall of the vascular structure.

If desired, working catheter 30 may be made detachable from the remainder of access system 5. This feature can be advantageous where longer term isolation of a vascular region is desired, e.g., for aneurysm embolization, since it allows the relatively large-bore working catheter to be removed, leaving only the zone isolation apparatus and fluid bypass apparatus present in the body lumen.

As noted above, proximal isolation barrier 10 and distal isolation barrier 15 are designed so as to be able to assume a diametrically-expanded configuration or a diametrically-reduced configuration. As also noted above, proximal isolation barrier 10 and distal isolation barrier 15 may comprise an inflatable/deflatable balloon or a compressible/expandable ring, etc. In this respect it should be appreciated that where proximal isolation barrier 10 and distal isolation barrier 15 comprise an inflatable/deflatable balloon, the balloon may extend across substantially the entire diameter of the vascular structure. Alternatively, the balloon may extend only about the periphery of the diameter of the vascular structure, and a membrane 67 may extend across the interior of the balloon, such as is shown in FIG. 3. A similar construction may be used where proximal isolation barrier 10 and distal isolation barrier 15 comprise a compressible/expandable ring, e.g., such as one formed from a superelastic shape memory alloy. Again, a membrane may extend across the interior of the ring.

Figures 7, 8, 9:
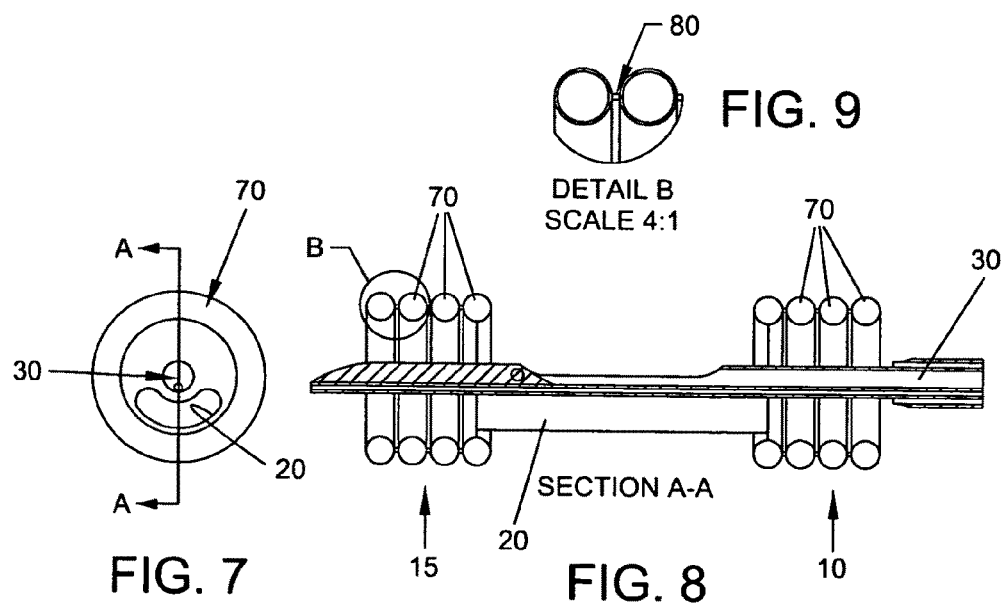
FIG. 7 is a schematic end view of the access system shown in FIG. 6.
FIG. 8 is a schematic sectional view taken along line A-A of FIG. 7.
FIG. 9 is a schematic enlarged view of the segment labeled B in FIG. 8.

FIGS. 6-9 show an alternative form of access system 5. The access system shown in FIGS. 6-9 is substantially the same as the access system shown in FIGS. 1-3 except that proximal isolation barrier 10 and distal isolation barrier 15 comprise multi-segmented balloons 70, and working catheter 30 includes an opening 75 connected to the lumen of working catheter 30. The use of these multi-segmented balloons 70 to form proximal isolation barrier 10 and distal isolation barrier 15 provide a wider, more stable barrier without restricting blood flow through bypass channel 20. As seen in FIG. 9, channels 80 may be provided between adjacent balloons so that the interior of the balloons are in communication with one another.

Figure 10:
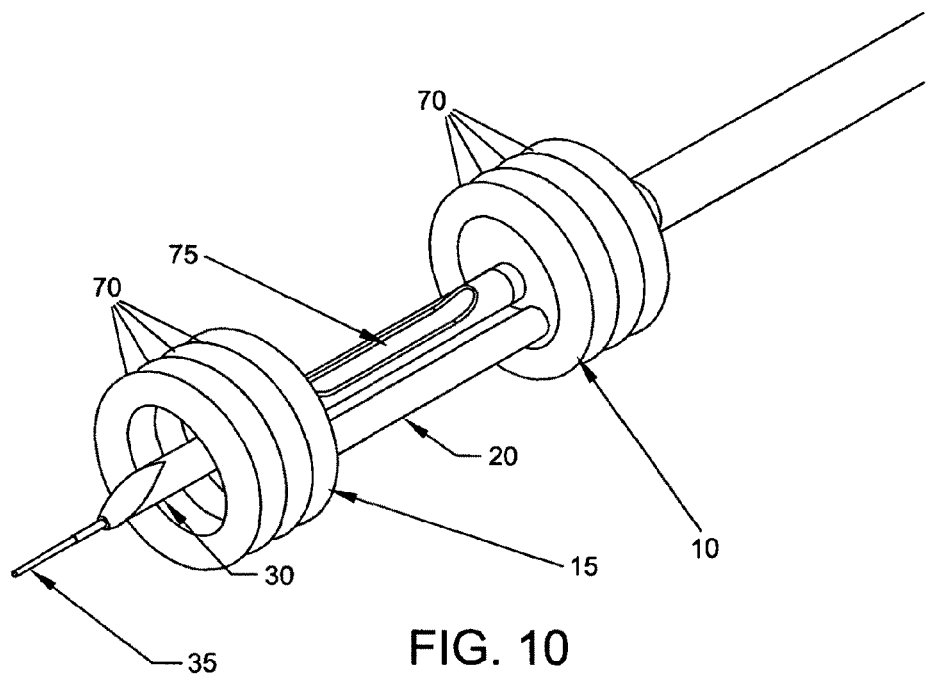
FIG. 10 is a schematic perspective view showing an alternative form of an access system.
Figures 11, 12:
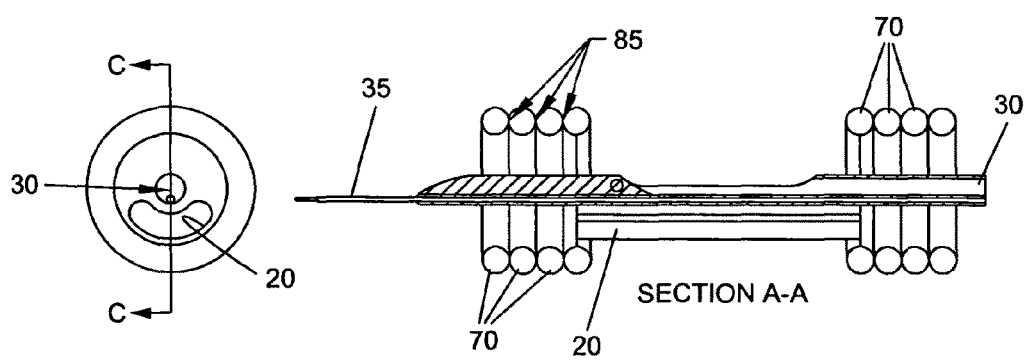
FIG. 11 is a schematic end view of the access system shown in FIG. 10.
FIG. 12 is a schematic sectional view taken along line C-C of FIG. 11.
Figure 13:
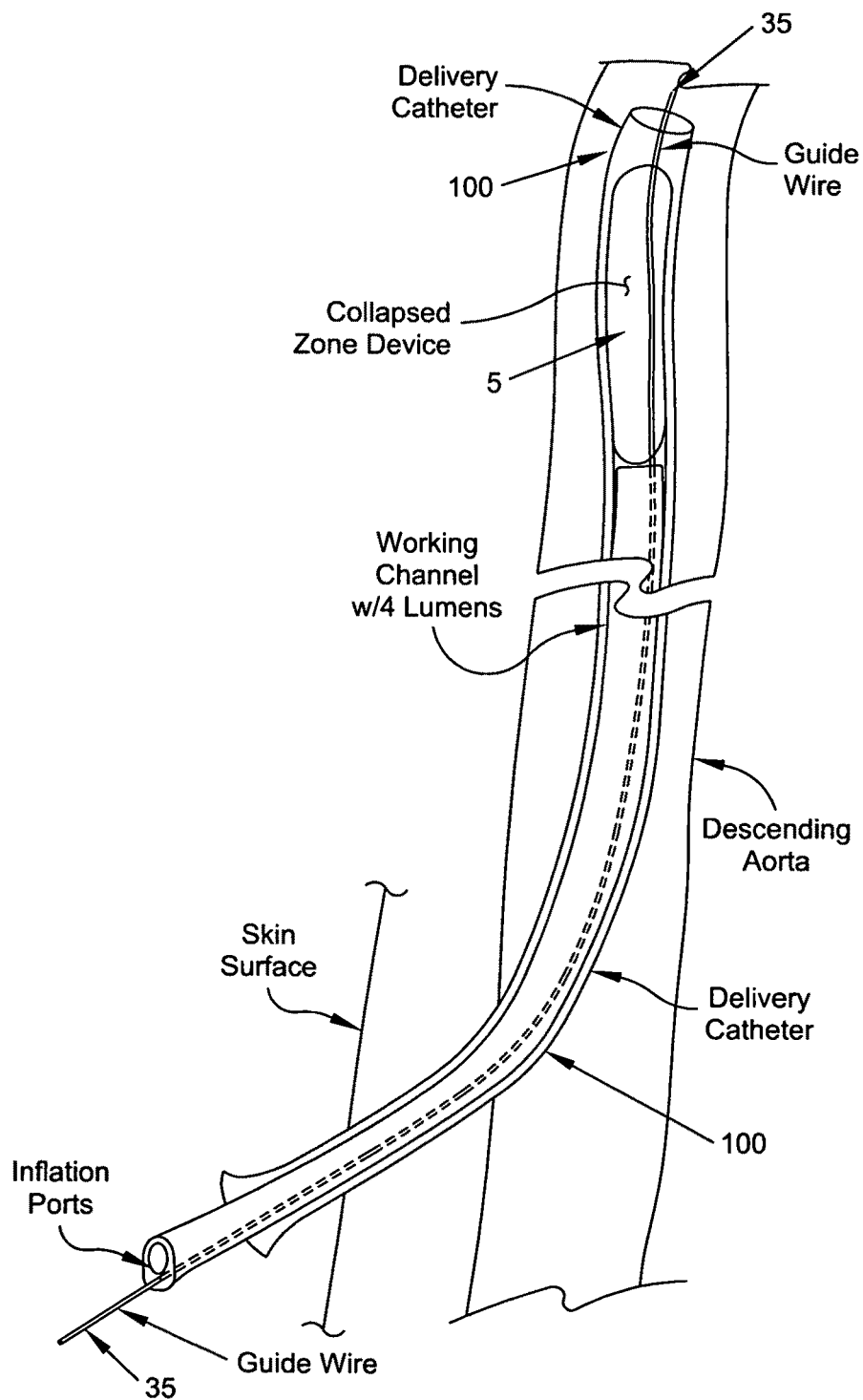

FIGS. 10-12 show an alternative form of access system 5. The access system shown in FIGS. 10-12 is substantially the same as the access system shown in FIGS. 6-9 except that channels 80 may be replaced with holes 85 so that the interior of the balloons are in communication with one another.

Deployment

Figure 14:
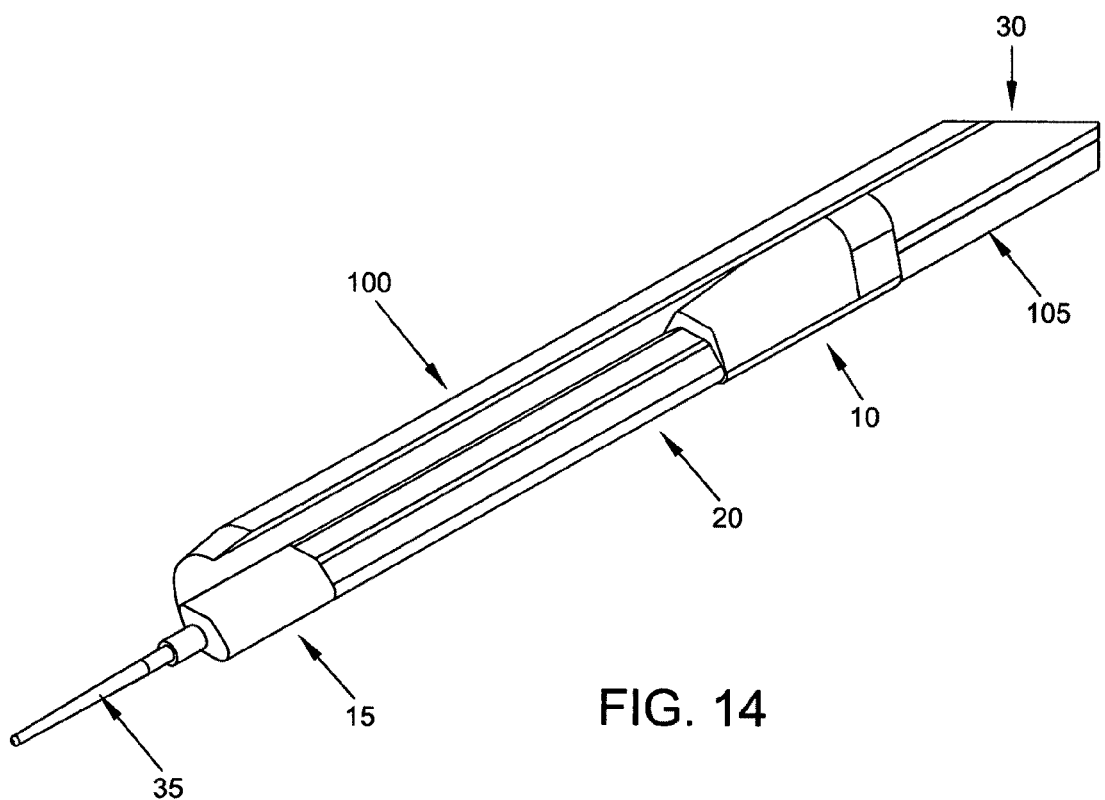
Figure 14A:
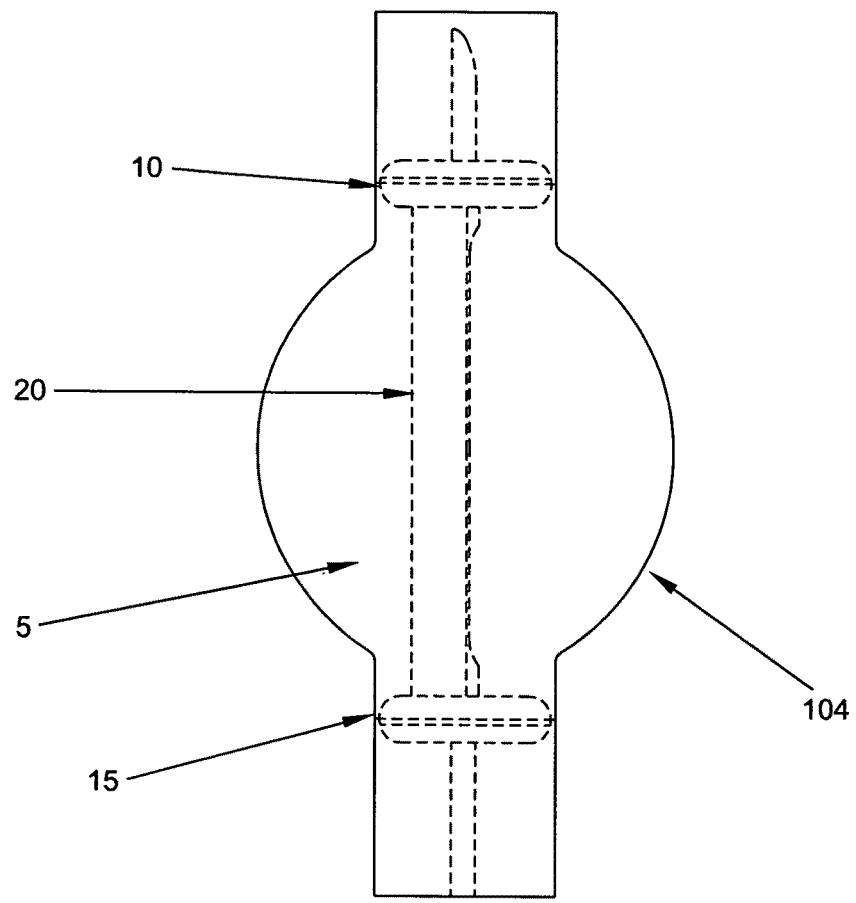
Figure 15:
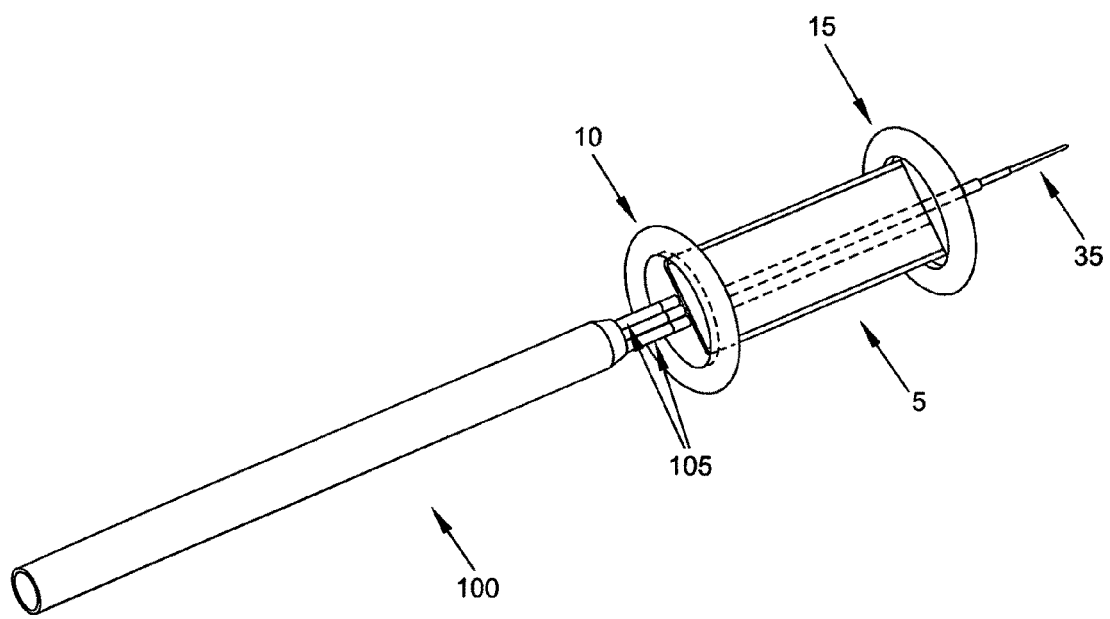
Figure 16:
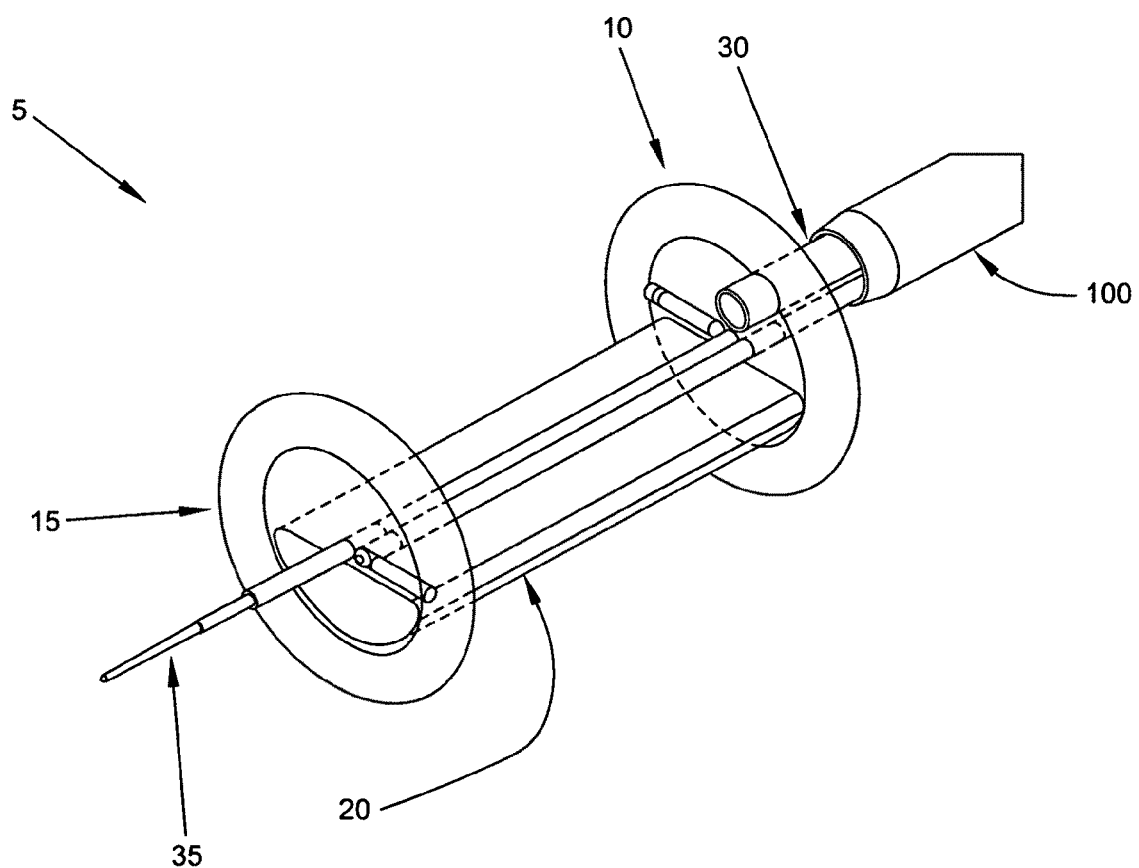
Figure 45:
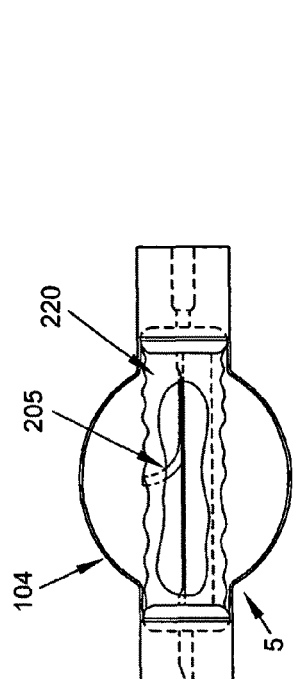
FIGS. 45-50 are schematic views showing another approach for repairing a fusiform aneurysm using an endoluminal approach and a flowable forming material.
Figure 46:
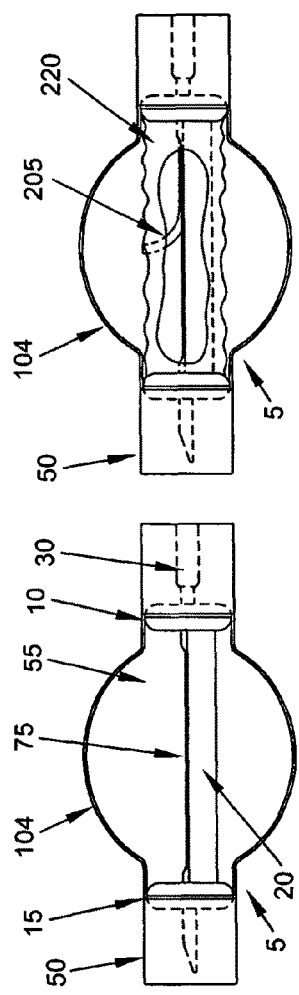
Figure 48:
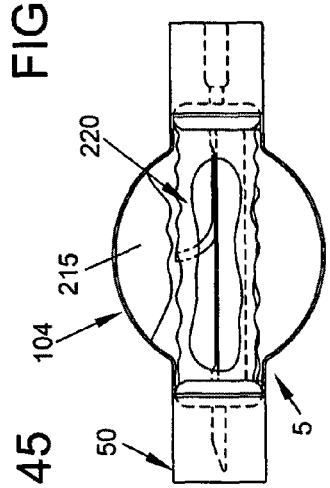
Figure 47:
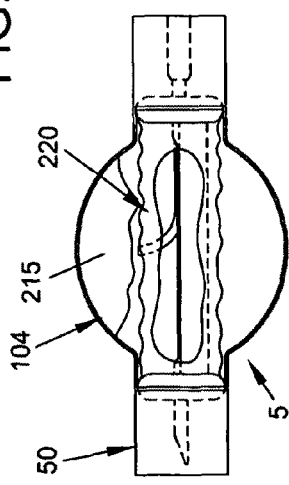
Figure 49:
Figure 50:
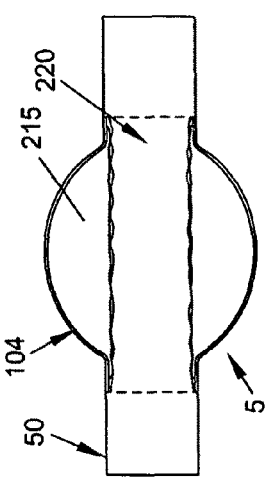

Access system 5 may be deployed in a vascular structure or other body lumen using a delivery catheter. More particularly, and looking next at FIGS. 13, 14, 14A and 15-20, a delivery catheter 100 comprising a delivery sheath 103 may be provided for advancing access system 5 to a procedure site within a vascular structure (or other body lumen), and for erecting access system 5 in the manner previously discussed. Furthermore, delivery catheter 100 may be used for advancing instruments down to the procedure site and/or removing debris from the procedure site (e.g., a fusiform aortic aneurysm 104 of the type shown in FIG. 14A), again in the manner previously discussed. Finally, delivery catheter 100 may be used to collapse access system 5 and remove it from the vascular structure (or other body lumen). In the case where access system 5 comprises inflatable/deflatable balloons in its proximal isolation barrier and/or distal isolation barrier 15, delivery catheter 100 may contain one or more fluid supply tubes 105 for inflating/deflating the balloons. It should be appreciated that delivery sheath 103 of delivery catheter 100 may also perform the function of an introducer sheath, in the sense that it can be secured to the exterior tissue of the patient once the delivery catheter is properly positioned. A hemostatic valve 110, with a side port 115, is preferably located on the proximal end of the delivery catheter to prevent the loss of blood through the catheter while still allowing the insertion of access system 5.

Anatomical Applications

It should be appreciated that access system 5 can be used to provide a wide range of therapies to vascular structures, e.g., aneurysm therapy, lesion therapy, infusion therapy, gene therapy, photodynamic therapy, etc. Access system 5 may also be used to repair tears, flaps and leaks in a vascular structure.

Furthermore, it should be also be appreciated that the present invention can be used to access structures other than vascular structures, e.g., the esophagus, stomach, small or large bowel, ureter, bladder, urethra, bronchus, bile duct, ear, nose, fallopian tube, other tubular or hollow structures within the human body, etc. In essence, the present invention can be advantageously used in substantially any body lumen where isolation, access and/or fluid bypass are desired. Additionally, it should be appreciated that the zone which is isolated between the proximal and distal isolation barriers could be of varying lengths, and of various diameters as well. Furthermore, many different catheter shapes and sizes may be utilized.

Without limiting the breadth and scope of the present invention, it is anticipated that the present invention is particularly well suited for treating fusiform aneurysms in the aorta and the larger peripheral blood vessels.

Furthermore, without limiting the breadth and scope of the present invention, it is anticipated that the present invention is particularly well suited for treating vascular trauma in a variety of situations where zone isolation and distal perfusion are both desirable and/or necessary, e.g., where vascular trauma needs to be temporarily stabilized while the patient is transported to another site for further treatment.

Method and Apparatus for Repairing Vascular Abnormalities and/or Other Body Lumen Abnormalities Using an Endoluminal Approach and a Flowable Forming Material In the foregoing description, there is disclosed a novel method and apparatus for endoluminally accessing the wall of a vascular structure or other body lumen while simultaneously providing zone isolation and fluid bypass capability.

Significantly, this novel method and apparatus for endoluminally accessing the wall of a vascular structure or other body lumen can be used in conjunction with another novel method and apparatus in order to endoluminally repair vascular abnormalities and/or other body lumen abnormalities. More particularly, in another aspect of the present invention, there is provided a novel method and apparatus for repairing vascular abnormalities and/or other body lumen abnormalities using an endoluminal approach and a flowable forming material.

Looking next at FIGS. 21-26, vascular structure 50 is shown having lateral aneurysm 45. As is well known, such a lateral aneurysm can present a substantial risk to the patient, since the aneurysm may enlarge and rupture if it is left untreated. To this end, it is generally desirable to block the flow of blood into the aneurysm so as to prevent the aneurysm from enlarging and rupturing. In some circumstances this may be accomplished by placing a clip across the neck of the aneurysm (i.e., via an invasive surgical approach), or by performing a repair with a graft (in the case of an abdominal aortic aneurysm). However, in other circumstances, it may be difficult to reach the aneurysm in order to apply the clip, e.g., where the aneurysm is located deep within the brain or in the case of trauma where no facilities are available in the field to perform a repair. In these situations, and others, it could be desirable to close off the aneurysm using an endoluminal approach. In this respect it should be appreciated that such an endoluminal approach can substantially reduce morbidity, since it eliminates the need to open the skull and avoids trauma to intervening tissue.

To this end, the present invention provides a novel method and apparatus for closing off an aneurysm using an endoluminal approach. More particularly, the present invention provides a method and apparatus for accessing an aneurysm via an endoluminal approach and then filling the aneurysm with a flowable forming material so as to close off the aneurysm from blood flow. Significantly, the present invention may also be used to endoluminally repair other vascular abnormalities and/or to repair other body lumen abnormalities such as vascular tears, flaps, and perforations using an endoluminal approach and a flowable forming material.

And significantly, the present invention may be facilitated using the aforementioned access system 5.

In accordance with one preferred form of the present invention, an aneurysm in a vascular structure may be repaired in the following manner. First, and still looking now at FIGS. 21-26, the aforementioned access system 5 is introduced into the vascular structure 50 and advanced along that vascular structure until erectable proximal isolation barrier 10 and erectable distal isolation barrier 15 straddle the neck of the aneurysm 45. Then proximal isolation barrier 10 and distal isolation barrier 15 are erected so as to isolate the segment of the vascular structure which is disposed between proximal isolation barrier 10 and distal isolation barrier 15 (i.e., isolation zone 55) from the remainder of the vascular structure. However, as this occurs, and as discussed previously, bypass channel 20 maintains fluid flow from one side of the isolation zone to the other side of the isolation zone. This is significant, since it permits uninterrupted oxygenation of downstream tissue, and hence permits procedure time to be increased without risk of oxygen deprivation to downstream tissue. The blood contained within isolation zone 55 (and aneurysm 45) may then be removed via opening 75 of working catheter 30 and replaced by another fluid, e.g., air, saline, etc. See FIG. 21. Next, a supply catheter 205 is advanced down working catheter 30 so that the distal end 210 of supply catheter 205 emerges from opening 75 and is disposed adjacent to, or within, aneurysm 45. See FIG. 22. Then a flowable forming material 215 is flowed out of distal end 210 of supply catheter 205 and into aneurysm 45. The flow of flowable forming material is continued until aneurysm 45 is, preferably, substantially completely filled with flowable forming material 215. See FIGS. 23-25. This flowable forming material 215 occupies the interior space of aneurysm 45 and prevents blood from flowing back into the aneurysm. Thereafter, after flowable forming material 215 has assumed its substantially stationary state, access system 5 is removed from vascular structure 50, allowing blood to return to the neck of aneurysm 45. However, since the aneurysm has been filled with flowable forming material 215, blood is unable to re-enter the aneurysm. Thus, the risk of subsequent aneurysm enlargement and rupture is significantly reduced.

It should be appreciated that inasmuch as access system 5 simultaneously provides both zone isolation capability and fluid bypass capability, access system 5 can be maintained in vascular structure 50 for substantial periods of time while flowable forming material 215 is deployed in position and assumes its substantially stationary state, thereby increasing the possibility of better repair and expanding the range of compositions which may be used for flowable forming material 215.

In FIGS. 21-26 discussed above, and FIGS. 27-32, 33-38, 39-44, 45-50, 51-56 and 57-63 which are hereinafter discussed, the boundary of flowable forming material 215 is generally shown to have a "wavy" boundary line. These are schematic views which are intended to indicate that the boundary line of flowable forming material 215 may or may not have a uniform, highly regular character, depending upon a variety of factors, e.g., the nature of the flowable forming material, the presence or absence of a mold structure (see below), the face of such a mold structure, etc. Thus, it should be understood that the use of a "wavy" boundary line in the drawings is not intended to necessarily indicate a non-uniform boundary line for flowable forming material 215. In point of fact, where flowable forming material 215 is intended to abut active blood flow, it is generally desired that flowable forming material 215 have a uniform, highly regular character in order to preserve laminar blood flow.

Flowable forming material 215 preferably comprises a bi-state material, having (i) a flowable state prior to disposition within the aneurysm, and (ii) a substantially stationary state after disposition within the aneurysm. In its flowable state, flowable forming material 215 may comprise a liquid, a foam, a gel, etc. Flowable forming material 215 may comprise a polymer which is cured in situ, an adhesive which hardens in situ, thrombus, fibrin glue, or any other material consistent with the present invention.

By way of example but not limitation, flowable forming material 215 may comprise a permanent, non-resorbable material. Some candidate permanent, non-resorbable materials are as follows:

(1) a hybrid inorganic/organic—hydraulic cement/polyurethane resin (expands slightly during cure), including:
  (a) a solid, rigid molded matrix;
  (b) a foaming during cure to produce an open-cell, microcellular, rigid foam; and
  (c) a syntactic foam containing pre-formed resorbable gelatin microspheres containing an active ingredient, such as an antibiotic;

(2) an organic polymer ambient temperature cure resin, including:
  (a) methyl methacrylate (MMA) liquid monomer catalyzed with peroxide initiator—this material can cure at body temperature within several minutes to several hours, depending upon catalyst type and amount, and has been successfully applied to knee replacement surgery, etc.—some available options include:
    (i) a solid, rigid molded poly(methyl methacrylate [PMMA] matrix;
    (ii) a syntactic foam containing pre-formed resorbable gelatin microspheres containing an active ingredient, such as an antibiotic; and
    (iii) an Oakes Foamer-produced pre-formed MMA liquid monomer foam injection to produce rigid, closed cell foam matrix—this material can expand slightly during cure within the body; and
  (b) polyurethane (non-resorbable) liquid pre-polymer blended and mixed with co-reactant polyol/catalyst component immediately prior to injection-molding into in-vivo mold cavity—this material can cure at body temperature within several minutes to several hours, depending upon catalyst type and amount, and biocompatible, non-resorbable polyurethane (PUR) monomers and catalysts are available that produce a soft, elastomeric-to-hard, rigid, cured PUR matrix—some available options include:
    (i) a solid, rigid molded matrix;
    (ii) a foaming during cure to produce an open-cell, microcellular, rigid foam—this non-resorbable foam matrix can be made to contain active components, such as antibiotics, that leach out at a controlled, adjustable rate;
    (iii) a syntactic foam containing pre-formed resorbable gelatin microspheres that are filled with an active ingredient, such as an antibiotic—as the gelatin capsule walls are resorbed into the body, the active ingredient becomes leached out in a controlled-release process that can be adjusted in rate and amount; and
    (iv) an Oakes Foamer-produced pre-formed PUR liquid monomer foam injection to produce rigid, closed cell foam matrix—this material can expand slightly during cure within the body.

By way of further example but not limitation, flowable forming material 215 may comprise a resorbable material. Some candidate resorbable materials are as follows:

(1) a resorbable organic polymer ambient temperature cure resin—some available options include:
  (a) a bioresorbable polyurethane (contains biodegradable chain segments) liquid pre-polymer blended and mixed with co-reactant polyol/catalyst component immediately prior to injection-molding into in-vivo mold cavity—this material cures at body temperature within several minutes to several hours, depending upon catalyst type and amount, and biocompatible, resorbable polyurethane (PUR) monomers and catalysts are available that produce soft, elastomeric-to-hard, rigid, cured PUR matrix—resorbable polyurethane polymer chain segments can be polylactic acid (PLA), polyglutaric acid (PGA), polyethylene oxide (PEO), polycaprolactone (PCL), polyvinyl alcohol (PVOH) and polyethylene/vinyl alcohol (EVOH) segments with tailorable resorption rates, varying from 15 days to 6 months, depending upon chain segment type and amount—some options include:
    (i) a solid, rigid molded matrix;
    (ii) a foaming during cure to produce an open-cell, microcellular, rigid foam—this in-vivo resorbable foam matrix can be made to contain active components, such as antibiotics, that are released into the body at a controlled, adjustable rate as the matrix is resorbed;
    (iii) a syntactic foam containing pre-formed resorbable gelatin microspheres that are filled with an active ingredient, such as an antibiotic—as resorbable polymer matrix and resorbable gelatin capsule walls are resorbed into the body, the active ingredient becomes leached out in a controlled-release process that can be adjusted in rate and amount; and
    (iv) an Oakes Foamer-produced pre-formed PUR liquid monomer foam injection to produce rigid, resorbable closed cell foam matrix—this material can expand slightly during cure within body; and
  (b) resorbable hydroxyethylmethacrylate ester (HEMAE) liquid monomer (this material contains biodegradable ester linkages, such as PLA, PCL and PGA linkages, attached to methacrylate monomer unit) catalyzed with peroxide initiator—this material can cure at body temperature within several minutes to several hours, depending upon catalyst type and amount—this material can undergo gradual bioresorption in-vivo—attached ester linkages can be functional groups, such as an antibiotic, that are released as ester linkage is hydrolyzed in-vivo—some options include:
    (i) a solid, rigid molded poly(HEMAE) matrix;
    (ii) a syntactic foam containing pre-formed resorbable gelatin microspheres containing an active ingredient, such as antibiotic; and
    (iii) an Oakes Foamer-produced pre-formed MMA liquid monomer foam injection to produce rigid, closed cell foam matrix—this material can expand slightly during cure within body.

In one preferred form of the invention, flowable forming material 215 comprises spider silk.

If desired, a mold structure can be erected within isolation zone 55 so as to restrain the flow of flowable forming material 215 while the forming material is still in its flowable state (and before the material transforms to its substantially stationary state). To this end, and looking now at FIGS. 27-31, there is shown a mold structure 220 for restraining the flow of flowable forming material 215 while the material transforms to its substantially stationary state. Mold structure 220 may be configured to line some or all of isolation zone 55, but in any case it lines at least the neck of the aneurysm. In FIGS. 27-31, mold structure 220 is configured to line substantially the entire periphery of isolation zone 55. In one preferred form of the invention, mold structure 220 is delivered to isolation zone 55 via access system 5, and is thereafter selectively detachable from the access system so that the mold structure can be left in vascular structure 50 upon withdrawal of access system 5. See FIG. 32. In another form of the invention, mold structure 220 may be permanently secured to access system 5 so that the mold structure is withdrawn from vascular structure 50 upon withdrawal of the access system. In either case, mold structure 220 forms a barrier about the neck of aneurysm 45 so as to prevent flowable forming material 215 from extravasating out of the body of aneurysm 45.

In one form of the invention, mold structure 220 preferably comprises a substantially continuous film such as is shown in FIGS. 27-32. In this form of the invention, distal end 210 of supply catheter 205 is preferably formed with a needle-like profile which permits the supply catheter to puncture through mold structure 220 so as to be able to deliver flowable forming material 215 into the interior of aneurysm 45. Alternatively, mold structure 220 can be formed with an opening therein which permits distal end 210 of supply catheter 205 to deliver flowable forming material into the interior of aneurysm 45. Furthermore, where mold structure 220 is to be left in place at the conclusion of the procedure, flowable forming material 215 and mold structure 220 can be configured to adhere to one another.

In another form of the invention, and looking now at FIGS. 33-38, mold structure 220 may comprise a mesh. This mesh has a porosity which is sufficiently small vis-à-vis the flow characteristics of flowable forming material 215 that the mesh restrains the flowable forming material within the aneurysm. Again, distal end 210 of supply catheter 205 is preferably formed with a needle-like profile which permits the supply catheter to puncture through mold structure 220 so as to be able to deliver flowable forming material 215 into the interior of aneurysm 45. Alternatively, mold structure 220 can be formed with an opening therein which permits distal end 210 of supply catheter 205 to deliver flowable forming material into the interior of aneurysm 45. And again, where mold structure 220 is to be left in place at the conclusion of the procedure, flowable forming material 215 and mold structure 220 can be configured to adhere to one another.

FIGS. 21-26, 27-32 and 33-38 all show the present invention being used in the context of repairing a lateral aneurysm. However, it is also possible to use the present invention to treat a fusiform aneurysm. See, for example, FIGS. 39-44, where the aneurysm is filled with flowable forming material 215 without using a mold structure; FIGS. 45-50, where the aneurysm is filled with flowable forming material 215 using a film-type mold structure 220, and FIGS. 51-56 where the aneurysm is filled with flowable forming material 215 using a mesh-type mold structure 220. Where the present invention is used to treat a fusiform aneurysm without the provision of a mold structure, it may be necessary to rotate working catheter 30 about its longitudinal axis so as to enable supply catheter 205 to deliver flowable forming material 215 to all aspects of the aneurysm. Where the present invention is used to treat a fusiform aneurysm with the provision of a mold structure 220, it may not be necessary to rotate working catheter 30 so as to enable supply catheter 205 to deliver flowable forming material 215 to all aspects of the aneurysm, although it may still be desirable to provide this option.

If desired, the flowable forming material 215 can be limited to the region of the aneurysm (e.g., as is shown in FIGS. 21-26, 27-32, 33-38, 39-44, 45-50 and 51-56), or it can be allowed to flow into a portion of the lumen of vascular structure 50 in order to provide a flange at the base of the solidified forming material 215. See, for example, FIGS. 57-63, which show a flange 225 formed integral with the solidified material filling aneurysm 45. In this respect it should be appreciated that flange 225 can be formed with or without a mold structure, e.g., a partial circumferential mold structure can be provided to constrain flowable forming material 215 so as to form flange 225 or the flowable forming material can be dispensed in a controlled manner so as to form flange 225. Again, FIGS. 57-63 show this concept in the context of a lateral aneurysm; however, is should be appreciated that this same concept may be applied to fusiform aneurysms as well.

Figure 64:
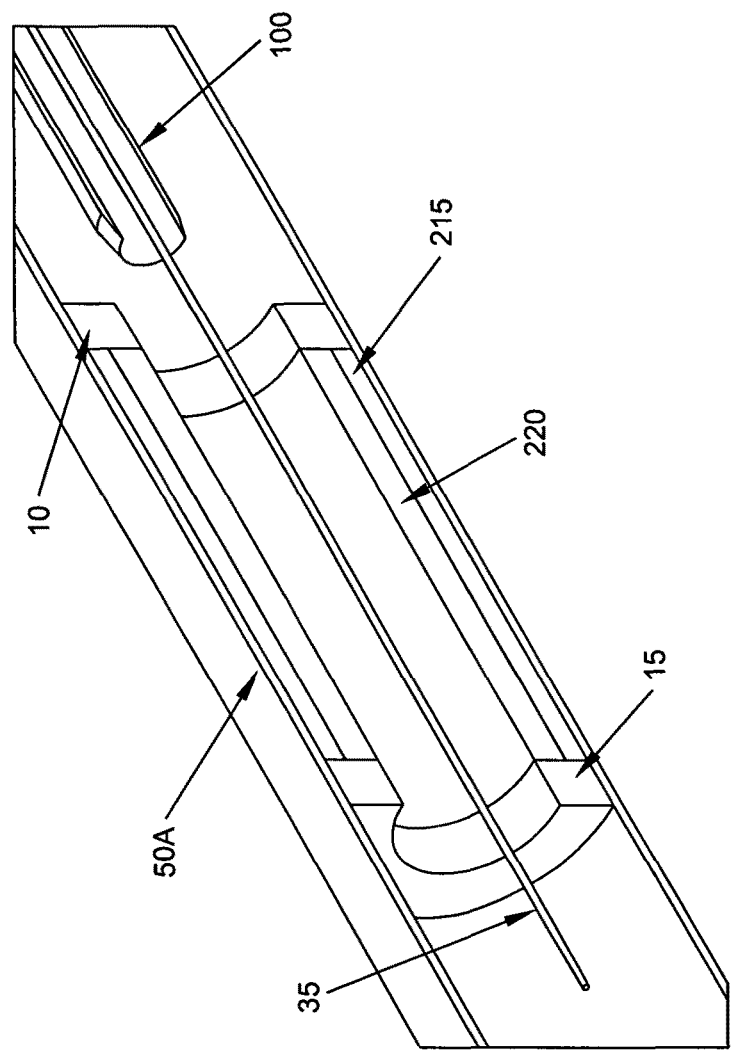
FIG. 64 is a schematic view showing an approach for repairing an abnormality in a body lumen using an endoluminal approach and a flowable forming material.

In the foregoing description, the present invention is discussed in the context of repairing an aneurysm in a vascular structure. However, it should be appreciated that the present invention may also be used to repair other types of vascular abnormalities (e.g., a blood vessel wall which is reduced in thickness or strength due to disease, trauma, therapeutic intervention such as an angioplasty, device failure such as leaks and/or migration of an abdominal aortic aneurysm (AAA) graft, etc.) and/or abnormalities in other body lumens (e.g., an intestinal wall which is reduced in thickness or strength due to disease or injury). Thus, for example, FIG. 64 shows a body lumen 50A which has flowable forming material 215 lining the wall of body lumen 50A. Also shown are a proximal isolation barrier 10, a distal isolation barrier 15 and a mold structure 220.

Figure 66:
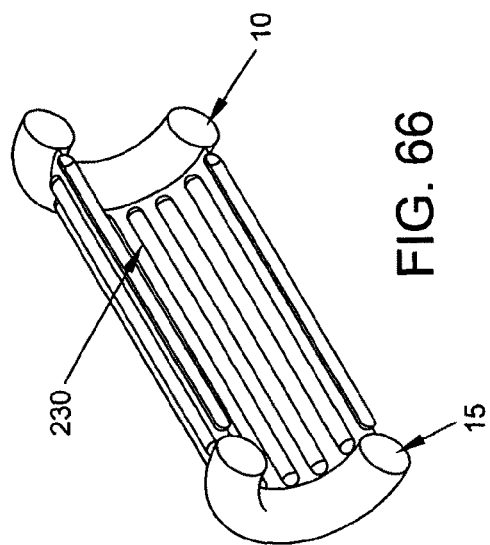
FIGS. 65-68 are schematic views showing various constructions for a mold structure which may be used in conjunction with the present invention.
Figure 68:
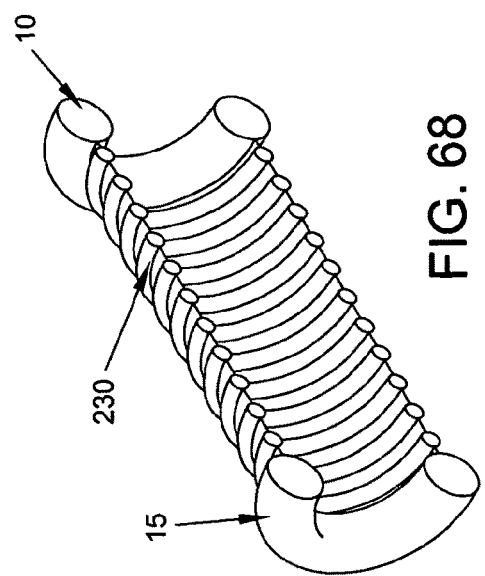
Figure 65:
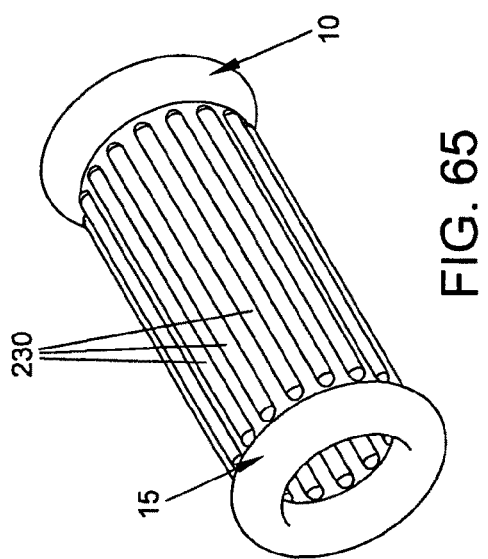
Figure 67:
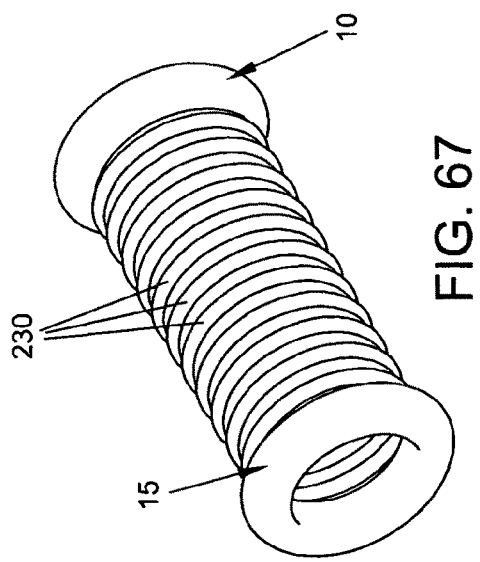

It should be appreciated that mold structure 220 can be provided with various configurations other than the simple continuous film configuration shown in FIGS. 27-32 and/or the simple mesh configuration shown in FIGS. 33-38. Thus, for example, mold structure 220 can be formed with longitudinally-extending ribs 230 (FIGS. 65 and 66), circumferentially-extending ribs 230 (FIGS. 67 and 68), and/or other configurations. If desired, where proximal isolation barrier 10 and distal isolation barrier 15 comprise inflatable balloon structures, the longitudinally-extending ribs 230 (FIGS. 65 and 66) and/or the circumferentially-extending ribs 230 (FIGS. 67 and 68) can also comprise balloons, which may or may not be in fluid communication with one or more of the balloons which form proximal isolation barrier 10 and distal isolation barrier 15.

Modifications

While the present invention has been described in terms of certain exemplary preferred embodiments, it will be readily understood and appreciated by one of ordinary skill in the art that it is not so limited, and that many additions, deletions and modifications may be made to the preferred embodiments discussed above while remaining within the scope of the present invention.

What is claimed is:

1. A method for repairing an abnormality in the wall of a body lumen, the method comprising:

providing an access system comprising:
- an erectable proximal isolation barrier capable of making a sealing engagement with the wall of the body lumen;
- an erectable distal isolation barrier capable of making a sealing engagement with the wall of the body lumen, the erectable distal isolation barrier being formed separately from the erectable proximal isolation barrier;
- a bypass channel secured to, and extending between, the proximal isolation barrier and the distal isolation barrier, the bypass channel comprising a lumen communicating with the region of the body lumen proximal to the proximal isolation barrier and with the region of the body lumen distal to the distal isolation barrier so that fluid can be passed from the region of the body lumen proximal to the proximal isolation barrier through the bypass channel and to the region of the body lumen distal to the distal isolation barrier;
- a working catheter passing through the proximal isolation barrier and into the region between the proximal isolation barrier and the distal isolation barrier, the working catheter providing a central lumen for providing access to the wall of the body lumen between the proximal isolation barrier and the distal isolation barrier;
- a supply catheter extendible out of the working catheter; and
- a mold structure extending between the proximal isolation barrier and the distal isolation barrier, the mold structure comprising a substantially continuous film;

isolating the abnormality in the wall of the body lumen from fluid flowing through the body lumen, while still allowing fluid to flow between the region of the body lumen proximal to the proximal isolation barrier and the region of the body lumen distal to the distal isolation barrier, by positioning the access system within the body lumen and erecting the distal isolation barrier and the proximal isolation barrier so that the proximal isolation barrier makes a sealing engagement with the wall of the body lumen proximal to the abnormality, the distal isolation barrier makes a sealing engagement with the wall of the body lumen distal to the abnormality, and the bypass channel provides the only fluid flow between the region of the body lumen proximal to the proximal isolation barrier and the region of the body lumen distal to the distal isolation barrier, with the mold structure isolating the abnormality from the region of the body lumen between the proximal isolation barrier and the distal isolation barrier, and with the mold structure following a cylindrical geometry so as to conform to the adjacent body lumen;

positioning flowable forming material adjacent to the abnormality in the wall of the body lumen by advancing the supply catheter out of the working catheter and through the mold structure and by passing the flowable forming material into the space between the wall of the body lumen and the mold structure; and transforming the flowable forming material into a substantially stationary state so as to repair the abnormality in the wall of the body lumen.

2. A method according to claim 1 wherein the body lumen comprises a vascular structure.

3. A method according to claim 1 wherein the body lumen comprises one from the group consisting of arterial structure, venous structure, other vascular structure, esophagus, stomach, small bowel, large bowel, ureter, bladder, urethra, bronchus, bile duct, ear, nose and fallopian tube.

4. A method according to claim 1 wherein the abnormality comprises an aneurysm.

5. A method according to claim 4 wherein the aneurysm comprises at least one from the group consisting of a fusiform aneurysm, a saccular aneurysm and a lateral aneurysm.

6. A method according to claim 4 wherein the aneurysm is located in one from the group consisting of the aorta, an iliac branch, a femoral artery, a cerebral artery and a carotid artery.

7. A method according to claim 4 wherein the flowable forming material is positioned within the interior of the aneurysm.

8. A method according to claim 7 wherein the flowable forming material is positioned within the interior of the aneurysm and within at least a portion of the interior of the body lumen.

9. A method according to claim 1 wherein the erectable proximal isolation barrier and the erectable distal isolation barrier are constructed so as to be capable of assuming a diametrically-reduced configuration and a diametrically-expanded configuration, and further wherein the erectable proximal isolation barrier and the erectable distal isolation barrier are in their diametrically-expanded configuration when making a sealing engagement with the wall of the body lumen.

10. A method according to claim 1 wherein at least one of the erectable proximal isolation barrier and the erectable distal isolation barrier comprises an upstream isolation barrier, and further wherein the upstream isolation barrier is configured to channel blood flow into the bypass channel.

11. A method according to claim 1 wherein the proximal isolation barrier comprises an inflatable/deflatable balloon.

12. A method according to claim 11 wherein the inflatable/deflatable balloon comprises a torus with a membrane closing off its center opening.

13. A method according to claim 11 wherein the proximal isolation barrier comprises a plurality of inflatable/deflatable balloons.

14. A method according to claim 13 wherein the balloons communicate with one another.

15. A method according to claim 1 wherein the proximal isolation barrier comprises a compressible/expandable superelastic shape memory alloy ring.

16. A method according to claim 15 wherein the compressible/expandable superelastic shape memory alloy ring comprises a torus with a membrane closing off its center opening.

17. A method according to claim 1 wherein the distal isolation barrier comprises an inflatable/deflatable balloon.

18. A method according to claim 17 wherein the inflatable/deflatable balloon comprises a torus with a membrane, closing off its center opening.

19. A method according to claim 17 wherein the distal isolation barrier comprises a plurality of inflatable/deflatable balloons.

20. A method according to claim 19 wherein the balloons communicate with one another.

21. A method according to claim 1 wherein the distal isolation barrier comprises a compressible/expandable superelastic shape memory alloy ring.

22. A method according to claim 21 wherein the compressible/expandable superelastic shape memory alloy ring comprises a torus with a membrane closing off its center opening.

23. A method according to claim 1 wherein the access system is deployed into the body lumen over a guidewire.

24. A method according to claim 1 comprising the additional step of detaching the working catheter from the proximal isolation barrier.

25. A method according to claim 1 further comprising removing debris from the body lumen.

26. A method according to 25 wherein the debris is removed while the proximal isolation barrier and the distal isolation barrier are erected.

27. A method according to 26 wherein the debris is removed by applying suction via the working catheter.

28. A method according to claim 25 wherein the erectable proximal isolation barrier is constructed so as to be capable of assuming a diametrically-reduced configuration and a diametrically-expanded configuration, wherein the erectable proximal isolation barrier is placed in its diametrically-expanded configuration when making a sealing engagement with the wall of the body lumen, and further wherein the erectable proximal isolation barrier is placed in its diametrically-reduced configuration before the debris is removed.

29. A method according to claim 1 wherein the native fluid located between the erectable distal isolation barrier and the erectable proximal isolation barrier is replaced with a substitute fluid.

30. A method according to claim 29 wherein the substitute fluid comprises saline.

31. A method according to claim 29 wherein the substitute fluid comprises air.

32. A method according to claim 29 wherein an endoscope is advanced to the zone located between the proximal isolation barrier and the distal isolation barrier via the working catheter.

33. A method according to claim 1 wherein the flowable forming material comprises a resorbable material.

34. A method according to claim 33 wherein the flowable forming material comprises a resorbable organic polymer ambient temperature cure resin.

35. A method according to claim 34 wherein the flowable forming material comprises at least one selected from the group consisting of a bioresorbable and a resorbable hydroxyethylmethacrylate ester (HEMAE) liquid monomer.

36. A method according to claim 1 wherein the substantially continuous film is in the form of a cylinder.

37. A method according to claim 1 wherein the mold structure comprises a circumferential configuration.

\* \* \* \* \*